US012788477B2

(12) United States Patent
Tschudy et al.

(10) Patent No.: US 12,788,477 B2
(45) Date of Patent: Nov. 10, 2026

(54) SURGICAL INSTRUMENT FOR USE IN SURGICAL ROBOTIC SYSTEMS

(71) Applicant: Covidien LP, Mansfield, MA (US)

(72) Inventors: Christopher T. Tschudy, Arvada, CO (US); Dylan R. Kingsley, Broomfield, CO (US); Andrew W. Zeccola, Salem, MA (US); Zachary T. Morgan, Boston, MA (US); Amanda M. Masotta, Canton, MA (US); Robert J. Stephens, Superior, CO (US); Sara A. Malang, Longmont, CO (US)

(73) Assignee: Covidien LP, Mansfield, MA (US)

( * ) Notice: Subject to any disclaimer, the term of this patent is extended or adjusted under 35 U.S.C. 154(b) by 162 days.

(21) Appl. No.: 18/708,257

(22) PCT Filed: Dec. 6, 2022

(86) PCT No.: PCT/US2022/051916
§ 371 (c)(1),
(2) Date: May 8, 2024

(87) PCT Pub. No.: WO2023/114045
PCT Pub. Date: Jun. 22, 2023

(65) Prior Publication Data

US 2025/0127555 A1 Apr. 24, 2025

Related U.S. Application Data

(60) Provisional application No. 63/337,631, filed on May 3, 2022, provisional application No. 63/290,260, filed on Dec. 16, 2021.

(51) Int. Cl.
*A61B 18/14* (2006.01)
*A61B 18/12* (2006.01)
(Continued)

(52) U.S. Cl.
CPC ...... *A61B 18/1445* (2013.01); *A61B 18/1206* (2013.01); *A61B 34/30* (2016.02);
(Continued)

(58) Field of Classification Search
CPC ............ A61B 18/1206; A61B 18/1445; A61B 2017/00389; A61B 2017/00973;
(Continued)

(56) References Cited

U.S. PATENT DOCUMENTS 6,132,368 A 10/2000 Cooper
6,206,903 B1 3/2001 Ramans
(Continued)

FOREIGN PATENT DOCUMENTS

EP 3278744 A1 2/2018
EP 3278753 A1 2/2018
EP 2713922 B1 8/2021

OTHER PUBLICATIONS

International Search Report and Written Opinion of the International Searching Authority issued in corresponding application PCT/US2022/051916 mailed Jun. 7, 2023 (27 pages).

*Primary Examiner* — Michael F Peffley
(74) *Attorney, Agent, or Firm* — Carter, DeLuca & Farrell, LLP

(57) ABSTRACT

A surgical system includes a robotic surgical system and a surgical instrument. The robotic surgical system includes at least one motor, at least one foot pedal, and a controller. The surgical instrument includes a pair of jaw members, a knife blade configured to cut tissue, and a drive assembly configured to cause the pair of jaw members to seal grasped tissue in response to actuation of the at least one foot pedal. The drive assembly is also configured to cause the knife blade to cut the tissue in response to actuation of the at least one foot pedal.

19 Claims, 11 Drawing Sheets

(51) Int. Cl.
*A61B 34/30* (2016.01)
*A61B 18/00* (2006.01)

(52) U.S. Cl.
CPC ............... *A61B 2018/00184* (2013.01); *A61B 2018/00601* (2013.01); *A61B 2018/0063* (2013.01); *A61B 2018/00642* (2013.01); *A61B 2018/00702* (2013.01); *A61B 2018/1455* (2013.01)

(58) Field of Classification Search
CPC ........... A61B 2018/00184; A61B 2018/00601; A61B 2018/0063; A61B 2018/00642; A61B 2018/00702; A61B 2018/1455; A61B 34/30; A61B 34/37; A61B 34/74
See application file for complete search history.

(56) References Cited

U.S. PATENT DOCUMENTS 6,246,200 B1 6/2001 Blumenkranz et al.
6,312,435 B1 11/2001 Wallace et al.
6,331,181 B1 12/2001 Tierney et al.
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.

(56) References Cited

U.S. PATENT DOCUMENTS 8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,043,027 B2 5/2015 Durant et al.
9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,165 B2 10/2018 Power
10,092,344 B2 10/2018 Mohr et al.
10,123,844 B2 11/2018 Nowlin
10,188,471 B2 1/2019 Brisson
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,426,467 B2 * 10/2019 Miller .................. A61B 5/0053
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.

(56) References Cited

U.S. PATENT DOCUMENTS

| | | | |
|---|---|---|---|
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 2010/0228250 | A1 | 9/2010 | Brogna |
| 2012/0310254 | A1* | 12/2012 | Manzo ................. A61B 17/072 606/130 |
| 2012/0316573 | A1* | 12/2012 | Durant ................... A61B 34/74 606/130 |
| 2013/0267950 | A1* | 10/2013 | Rosa .............. A61B 17/320016 606/45 |
| 2019/0365458 | A1 | 12/2019 | Whitlock et al. |

* cited by examiner

SURGICAL INSTRUMENT FOR USE IN SURGICAL ROBOTIC SYSTEMS

CROSS REFERENCE TO RELATED APPLICATIONS

This application is a U.S. National Stage Application filed under 35 U.S.C. § 371(a) of International Patent Application No. PCT/US2022/051916, filed on Dec. 6, 2022, which claims the benefit of and priority to provisional U.S. Patent Application No. 63/290,260, filed on Dec. 16, 2021, and provisional U.S. Patent Application No. 63/337,631, filed on May 3, 2022. The entire contents of the foregoing applications are incorporated by reference herein.

FIELD

This disclosure relates to surgical instruments and, more specifically, to a surgical instrument capable of grasping, treating, and cutting tissue for use in surgical robotic systems.

BACKGROUND

Robotic surgical systems are increasingly utilized in various surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be given to determining how to utilize the available inputs provided by the robotic arm to achieve the desired functionality of the surgical instrument.

SUMMARY

As used herein, the term “distal” refers to the portion that is being described which is further from an operator (whether a human surgeon or a surgical robot), while the term “proximal” refers to the portion that is being described which is closer to the operator. Terms including “generally,” “about,” “substantially,” and the like, as utilized herein, are meant to encompass variations, e.g., manufacturing tolerances, material tolerances, use and environmental tolerances, measurement variations, design variations, and/or other variations, up to and including plus or minus 10 percent.

As used herein, the term “clinician” refers to any medical professional (i.e., doctor, surgeon, nurse, or the like) or other user involved in operation of the surgical system described herein.

Provided in accordance with aspects of this disclosure is a surgical system. The surgical system includes a robotic surgical system and a surgical instrument. The robotic surgical system includes at least one motor, at least one foot pedal, and a controller in communication with the at least one foot pedal. The controller is configured to cause the at least one motor to provide an input based on actuation of the at least one foot pedal. The surgical instrument is in communication with the robotic surgical system and includes a pair of jaw members, a knife blade, and a drive assembly. The pair of jaw members are movable between a spaced-apart position and an approximated position and are configured to deliver electrosurgical energy to tissue grasped between the pair of jaw members to seal the tissue when the pair of jaw members are in the approximated position. The knife blade is configured to extend through the pair of jaw members to cut tissue grasped between the pair of jaw members when the pair of jaw members are in the approximated position. The drive assembly is configured to receive the input provided by the at least one motor. The drive assembly is also configured to cause the pair of jaw members to deliver energy to the tissue grasped between the pair of jaw members to seal the tissue in response to a first actuation of the at least one foot pedal. The drive assembly is also configured to cause the knife blade to extend through the pair of jaw members to cut the tissue in response to a determination that the tissue has been sealed, a determination that the pair of jaw members are maintained in the approximated position, and a second actuation of the at least one foot pedal within a predetermined period of time following the first actuation of the at least one foot pedal.

In an aspect of this disclosure, the first actuation of the at least one foot pedal includes maintaining the at least one foot pedal in an actuated position.

In another aspect of this disclosure, the second actuation of the at least one foot pedal includes a single-tap of the at least one foot pedal.

In another aspect of this disclosure, the determination that the tissue has been sealed is based on the first actuation of the at least one foot pedal and a termination of the first actuation of the at least one foot pedal.

In still another aspect of this disclosure, the predetermined period of time is about 15 seconds.

In yet another aspect of this disclosure, the predetermined period of time is from about 0.5 seconds to about 15 seconds.

In still another aspect of this disclosure, the predetermined period of time is from about 0.75 seconds to about 15 seconds.

In another aspect of this disclosure, the second actuation of the at least one foot pedal includes actuating the same foot pedal as the first actuation of the at least one foot pedal.

In yet another aspect of this disclosure, the at least one foot pedal includes at least two foot pedals, and the second actuation of the at least one foot pedal includes actuating a different foot pedal than the foot pedal actuated by the first actuation of the at least one foot pedal.

In an aspect of this disclosure, the determination that the pair of jaw members are maintained in the approximated position is based on a position of a drive rod configured to be actuated longitudinally to move the pair of jaw members between the spaced-apart and approximated positions.

In another aspect of this disclosure, the robotic surgical system includes a handle controller configured to cause the pair of jaw members to transition between the spaced-apart position and the approximated position to grasp tissue between the pair of jaw members or release tissue from between the pair of jaw members.

In still another aspect of this disclosure, the surgical system also includes an electrosurgical energy source configured to deliver the electrosurgical energy to the end effector assembly.

In still yet another aspect of this disclosure, the electrosurgical energy source is configured to determine that the tissue is sealed and to provide an indication that the tissue is sealed.

A method provided in accordance with this disclosure includes manipulating an end effector assembly of a surgical instrument to grasp tissue. The method also includes receiving a first actuation of a first foot pedal, causing the end effector assembly to deliver energy to the tissue to seal the tissue in response to the first actuation, and releasing the foot pedal to terminate the first actuation in response to an indication that the tissue is sealed. The method also includes receiving a second actuation of the first foot pedal or a second foot pedal and causing a knife blade of the surgical instrument to cut the tissue or not cut the tissue based on a releasing of the first foot pedal to terminate the first actuation, a determination that the end effector is grasping the tissue, and receiving the second actuation within a predetermined period of time following the receiving of the first actuation of the first foot pedal.

In an aspect of this disclosure, receiving the first actuation of the first foot pedal includes maintaining the first foot pedal in an actuated position.

In another aspect of this disclosure, receiving the second actuation of the first or second foot pedal includes providing a single-tap actuation of the first or second foot pedal.

In still another aspect of this disclosure, the predetermined period of time is about 15 seconds.

In still yet another aspect of this disclosure, the predetermined period of time is from about 0.5 seconds to about 15 seconds.

In yet another aspect of this disclosure, the predetermined period of time is from about 0.75 seconds to about 15 seconds.

In another aspect of this disclosure, the determination that the end effector is grasping the tissue is based on a position of a drive rod configured to be actuated longitudinally to move the end effector between an open position and a closed position.

In still another aspect of this disclosure, releasing of the first foot pedal to terminate the first actuation indicates that the tissue is sealed.

Another surgical system provided in accordance with this disclosure includes a robotic surgical system and a surgical instrument. The robotic surgical system includes at least one controller, at least one foot pedal, and a controller. The controller is in communication with the at least one foot pedal and is configured to cause the at least one motor to provide an input based on actuation of the at least one foot pedal. The surgical instrument is in communication with the robotic surgical system and includes a pair of jaw members, a knife blade, and a drive assembly. The pair of jaw members are movable between a spaced-apart position and an approximated position and configured to deliver electrosurgical energy to tissue grasped between the pair of jaw members to seal the tissue when the pair of jaw members are in the approximated position. The knife blade is configured to extend through the pair of jaw members to cut tissue grasped between the pair of jaw members when the pair of jaw members are in the approximated position. The drive assembly is configured to receive the input provided by the at least one motor. The drive assembly is also configured to cause the pair of jaw members to deliver energy to the tissue grasped between the pair of jaw members to seal the tissue in response to maintaining the at least one foot pedal in an actuated position. The drive assembly is also configured to cause the knife blade to extend through the pair of jaw members to cut the tissue in response to a release of the at least one foot pedal from the actuated position, a determination that the pair of jaw members have not moved from the approximated position toward the spaced-apart position, and a single-tap actuation of the at least one foot pedal within a predetermined period of time following movement of the at least one foot pedal to the actuated position to initiate delivery of the energy to the tissue grasped between the jaw members to seal the tissue.

Another surgical system provided in accordance with this disclosure includes a robotic surgical system and a surgical instrument. The robotic surgical system includes a robot arm including at least one operable interface configured to provide an input, at least one motor, an actuation device, and a controller in communication with the actuation device and configured to control the at least one motor to provide the input to the at least one operable interface. The surgical instrument includes an end effector assembly having a pair of jaw members configured to deliver electrosurgical energy to tissue grasped between the pair of jaw members to seal tissue. The surgical instrument also includes a knife blade and a drive assembly. The knife blade is configured to extend through the pair of jaw members to cut tissue grasped between the pair of jaw members. The drive assembly is configured to operably couple with the at least one operable interface to receive the input therefrom. The drive assembly, in response to a single actuation of the actuation device, is configured to cause the pair of jaw members to deliver energy to the tissue grasped between the jaw members to seal the tissue and to cause the knife blade to extend through the pair of jaw members to cut the tissue after the tissue is sealed.

In an aspect of this disclosure, the actuation device is a foot pedal configured to be moved between an unactuated position and an actuated position.

In another aspect of this disclosure, the robotic surgical system includes a handle controller configured to cause the pair of jaw members to transition between a spaced-apart position and an approximated position to grasp tissue between the pair of jaw members or release tissue from between the pair of jaw members.

In another aspect of this disclosure, the single actuation of the actuation device is further configured to cause the pair of jaw members to transition from an approximated position to a spaced-apart position to release the tissue from the pair of jaw members after the tissue is cut.

In still another aspect of this disclosure, an additional actuation of the actuation device that is independent from the single actuation of the actuation device is further configured to cause the pair of jaw members to transition from the approximated position to the spaced-apart position after the tissue is cut.

In yet another aspect of this disclosure, wherein the robotic surgical system includes a handle controller configured to enable manipulation of the end effector assembly to position the tissue between the pair of jaw members when the jaw members are in a spaced-apart position.

In another aspect of this disclosure, the single actuation of the actuation device is further configured to cause the knife blade to cut the tissue based on a determination that the tissue is sealed and the knife blade to not cut the tissue based on a determination that the tissue is not sealed.

In yet another aspect of this disclosure, the surgical system includes an electrosurgical energy source configured to deliver the electrosurgical energy to the end effector assembly.

In another aspect of this disclosure, the electrosurgical energy source is configured to determine that the grasped tissue is sealed, and extending of the knife blade through the pair of jaw members to cut the tissue after the tissue is sealed is based on the determination that the tissue is sealed.

A method provided in accordance with this disclosure includes manipulating an end effector assembly of a surgical instrument to grasp tissue. The method also includes receiving a single actuation of a foot pedal. The method also includes, in response to the single actuation, causing the end effector assembly to deliver energy to the tissue to seal the tissue, determining if the tissue is sealed, and in response to determining if the tissue is sealed, causing a knife blade of the surgical instrument to cut the tissue or not cut the tissue.

In an aspect of this disclosure, the method also includes determining if the tissue is grasped by the end effector assembly.

In another aspect of this disclosure, the method also includes, in response to the single actuation, causing the knife blade of the surgical instrument to cut the tissue based on a determination that the tissue is sealed and causing the knife blade of the surgical instrument to not cut the tissue based on a determination that the tissue is not sealed.

In still another aspect of this disclosure, the method also includes, in response to the single actuation, determining if the tissue is cut and in response to determining if the tissue is cut, causing the end effector assembly to release the tissue or not release the tissue.

In still yet another aspect of this disclosure, manipulating the end effector assembly of the surgical instrument to grasp tissue is in response to actuation of a handle controller.

In another aspect of this disclosure, the method also includes receiving an instruction to manipulate the end effector assembly to position the tissue relative to the end effector assembly before grasping the tissue.

In still another aspect of this disclosure, the method also includes receiving an instruction to operate the surgical instrument in an auto-cut mode.

Another surgical system provided in accordance with this disclosure includes a robotic surgical system and a surgical instrument. The robotic surgical system includes a robot arm including at least one operable interface configured to provide an input, at least one motor, a foot pedal, and a controller in communication with the foot pedal and configured to control the at least one motor to provide the input to the at least one operable interface in response to actuation of the foot pedal. The surgical instrument is configured to be operated by the robotic surgical system in one of a manual mode or an auto-cut mode. The surgical instrument includes an end effector assembly having a pair of jaw members configured to deliver electrosurgical energy to tissue grasped between the pair of jaw members to seal the tissue and a knife blade configured to extend through the pair of jaw members to cut the tissue grasped between the pair of jaw members. The surgical instrument also includes a drive assembly configured to operably couple with the at least one operable interface to receive the input therefrom. The drive assembly, in response to a received instruction to operate the surgical instrument in the auto-cut mode and a single actuation of the foot pedal, is configured to cause the pair of jaw members to deliver energy to the tissue after the tissue is grasped therebetween to seal the tissue and the knife blade to extend through the pair of jaw members to cut the tissue based on a determination that the tissue is sealed.

In an aspect of this disclosure, the single actuation of the actuation device is further configured to cause the knife blade to cut the tissue based on the determination that the tissue is sealed and the knife blade to not cut the tissue based on a determination that the tissue is not sealed.

In another aspect of this disclosure, the single actuation of the foot pedal is further configured to cause the pair of jaw members to transition from an approximated position to a spaced-apart position to release the tissue from the pair of jaw members after the tissue is cut.

In still another aspect of this disclosure, the robotic surgical system includes a handle controller configured to cause the pair of jaw members to transition between a spaced-apart position and an approximated position to grasp tissue between the pair of jaw members or release tissue from between the pair of jaw members.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figure 1:
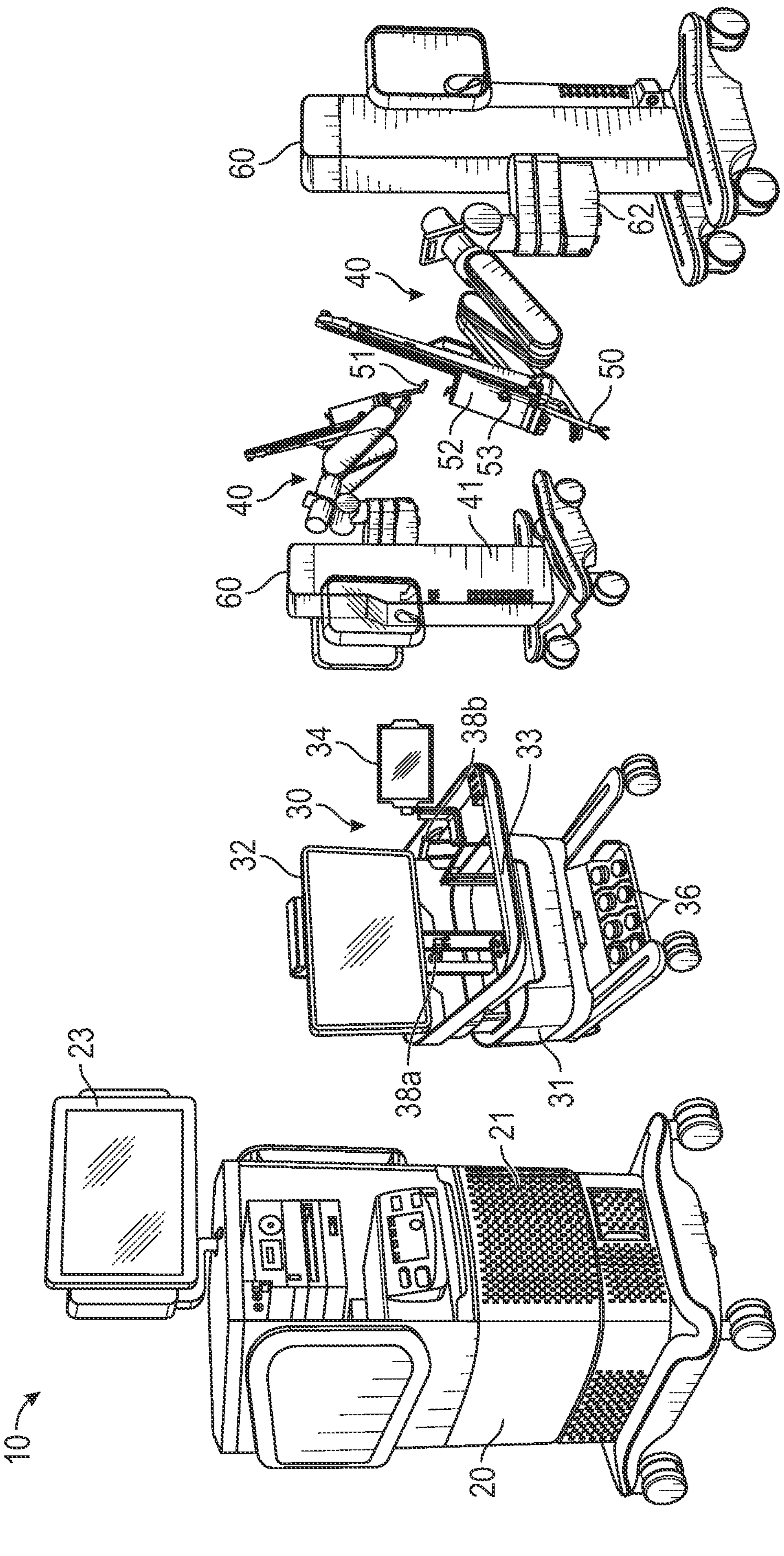
FIG. 1 is a schematic illustration of a surgical robotic system including a control tower, a console, and one or more surgical robotic arms according to aspects of this disclosure.

Provided in accordance with aspects of this disclosure is a surgical system including a surgical instrument for use with a robotic surgical system. The surgical instrument includes a housing, a shaft extending distally from the housing, and an end effector assembly disposed at a distal end of the shaft. The end effector assembly includes first and second jaw members. At least the first jaw member is movable relative to the second jaw member to grasp tissue therebetween. The end effector assembly is configured to receive electrosurgical energy from an electrosurgical energy source for sealing tissue grasped between the first and second jaw members. The surgical instrument also includes a knife blade configured to cut tissue following the completion of a tissue sealing cycle. In aspects of this disclosure, grasping, sealing, cutting, and/or releasing of tissue may be acheived by operation of one or more actuation devices (e.g., foot pedal, handle controller, hand controller button, GUI controller, voice activation, etc.) of a robotic surgical system. Standard robotic surgical systems may involve a first actuation of a foot pedal to start the tissue sealing cycle and, following the conclusion of the tissue sealing cycle, multiple subsequent actuations of a foot pedal (e.g., a "double-tap") may be used to achieve tissue cutting. The use of multiple actuations of a foot pedal to effect tissue cutting is intended to ensure that the clinician intends for tissue to be cut and to avoid accidental cutting of tissue caused by a single actuation (e.g., "a single-tap") of a foot pedal. While this approach helps to avoid accidental or unintended cutting of tissue, it may be slow and burdensome for the clinician to double-tap a foot pedal with their foot during a procedure. This disclosure improves the user flow for the clinician operating the robotic surgical system by having the clinician perform as few steps as possible to effect tissue cutting following the completion of a tissue sealing cycle provided that one or more criteria are satisfied. Satisfying certain criteria prior to cutting of tissue ensures that the tissue sealing cycle is complete and that it is safe for the tissue to be cut. In accordance with this disclosure, if certain criteria have been satisfied indicating that the tissue sealing cycle is complete and that it is safe for the sealed tissue to be cut, the user flow for the clinician may be sped up by requiring only a single actuation of an actuation device to achieve a tissue cut following the completion of a tissue sealing cycle. In some embodiments of this disclosure, the user flow for the clinician may be sped up in this scenario by requiring only a single actuation of a foot pedal (e.g., a "single-tap") to achieve a tissue cut following the completion of a tissue sealing cycle. In one example, the single-tap criteria include: i) a determination that the tissue sealing cycle is complete; ii) maintaining of the end effector in the closed position and grasping the tissue that has been sealed; and iii) receiving a "single-tap" of a foot pedal within a predetermined period of time (e.g., less than 15 seconds, between about 0.75 seconds and about 15 seconds, or between about 0.5 seconds and about 15 seconds) following initiation of the tissue sealing cycle or following completion of the tissue sealing cycle.

In aspects of this disclosure, a determination that a tissue sealing cycle is complete may be based on a first actuation of a foot pedal to start the tissue sealing cycle and a subsequent releasing of that foot pedal to terminate the first actuation at the conclusion of the tissue sealing cycle. This is an indication that the energy source has been activated to deliver energy to the end effector and is no longer activated. For example, in response to an indication (e.g., generated by the energy source) that a tissue sealing cycle is complete, a clinician is likely in this scenario to release the actuated foot pedal to terminate a demand for the energy source to deliver energy to the end effector. The indication may be any indication suitable to alert the clinician that the tissue sealing cycle is complete. Examples of such an indication include, but are not limited to, an audible tone, a visual graphic, or the like. In aspects of this disclosure, the energy source will automatically terminate delivery of energy to the end effector of the surgical instrument at the conclusion of a tissue sealing cycle regardless of whether or not the foot pedal remains actuated. Once the tissue sealing cycle is complete and the clinician releases the foot pedal, if the end effector remains in a closed position to grasp the sealed tissue between the jaw members (or has otherwise not been moved toward an open position) and the clinician actuates a foot pedal with a single-tap (e.g., using the same foot pedal that was actuated to effect the tissue sealing cycle or using a different foot pedal) within a predetermined period of time, the knife blade is caused to cut the sealed tissue. In aspects of this disclosure, the predetermined period of time may be initiated by the first actuation of the foot pedal to start the tissue sealing cycle. For example, if the clinician single-taps the foot pedal within a predetermined period of time following initiation of the tissue sealing cycle (e.g., via the first actuation of the foot pedal), the knife blade is caused to cut the sealed tissue if the other aforementioned single-tap criteria are satisfied. In other aspects, the predetermined period of time may be initiated by the determination that a tissue sealing cycle is complete (e.g., by release of the foot pedal that started the tissue sealing cycle). Satisfaction of the aforementioned single-tap criteria is an indication that the tissue is sealed, that it is safe to cut the tissue, and that the clinician intends for the sealed tissue to be cut. The above-described operation of the surgical instrument helps to decrease procedure time, improve the user flow, and prevent cutting of tissue prior to completion of a tissue seal. It should be understood that, in some embodiments of this disclosure, the aforementioned single-tap of the foot pedal may be replaced by a single actuation of a different actuation device of the disclosed surgical system such as, for example, a handle controller, a hand controller button, a paddle controller, a GUI controller, voice activation, etc.

In another aspect of this disclosure, the surgical instrument may be configured for use in both a manual mode, enabling selective manual actuation of the end effector assembly for grasping, treating, and/or cutting tissue, and an automatic mode or "auto-cut" mode, enabling grasping, treating, cutting, and/or releasing of tissue to be automatically and repeatedly effected. In aspects of this disclosure, grasping, treating, cutting, and/or releasing of tissue may be automatically effected via feedback-based control. Operation of the surgical instrument in auto-cut mode helps to decrease procedure time, improve the user flow experience, and prevent cutting of tissue prior to completion of a tissue seal.

As described in detail below, the surgical instruments of this disclosure are configured for use with a surgical robotic system, which may include, for example, a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which, in turn, move the robotic arm in response to the movement command. Those skilled in the art will understand that this disclosure, although described in connection with surgical robotic systems, may also be adapted for use with endoscopic surgical instruments and/or open surgical instruments.

With reference to FIG. 1, a surgical robotic system 10 includes a control tower 20, which is connected to components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The one or more surgical instruments 50 may be configured for use during minimally invasive surgical procedures and/or open surgical procedures. In aspects, one of the surgical instruments 50 may be an energy-based surgical instrument such as, for example, an electrosurgical end effector assembly 140 (FIG. 5A) configured to seal tissue by grasping tissue between a pair of jaws and applying electrosurgical energy, and to cut the sealed tissue using a mechanical cutter or, alternatively, an energy-based cutter. In further aspects, one of the surgical instruments 50 may be an ultrasonic sealing and dissection instrument configured to seal tissue by grasping tissue between opposing structures and applying ultrasonic energy thereto. In still further aspects, one of the surgical instruments 50 may be a surgical stapler including a pair of jaws configured to clamp tissue, deploy a plurality of tissue fasteners, e.g., staples, through the clamped tissue, and/or to cut the stapled tissue. In yet further aspects, one of the robotic arms 40 may include an endoscope camera 51 configured to capture video of the surgical site. The surgical console 30 includes a first display 32, which is configured to display a video feed of the surgical site provided by endoscope camera 51 of the surgical instrument 50 disposed on the robotic arm 40, and a second display 34, which is configured to display a user interface for controlling the surgical robotic system 10. The first and second displays 32 and 34 are touchscreens allowing for displaying of various graphical user inputs such as, for example, a mode selection feature that allows the clinician to select between modes of operation (e.g., manual mode, auto-cut mode, etc.).

The surgical console 30 also includes a plurality of actuation devices, such as foot pedals 36, which are used by a user to remotely control surgical instrument 50 and/or robotic arms 40, and/or a pair of handle controllers 38*a* and 38*b* which are used by a user to remotely control robotic arms 40 and/or surgical instrument 50. The surgical console may further include an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement and/or actuation sequence in response to input from the foot pedals 36 and the handle controllers 38*a* and 38*b*.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by this disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth® (an open wireless protocol for exchanging data over short distances, using short length radio waves, from fixed and mobile devices, creating personal area networks (PANs)), ZigBee® (a specification for a suite of high level communication protocols using small, low-power digital radios based on the IEEE 122.15.4-2003 standard for wireless personal area networks (WPANs))

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in this disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
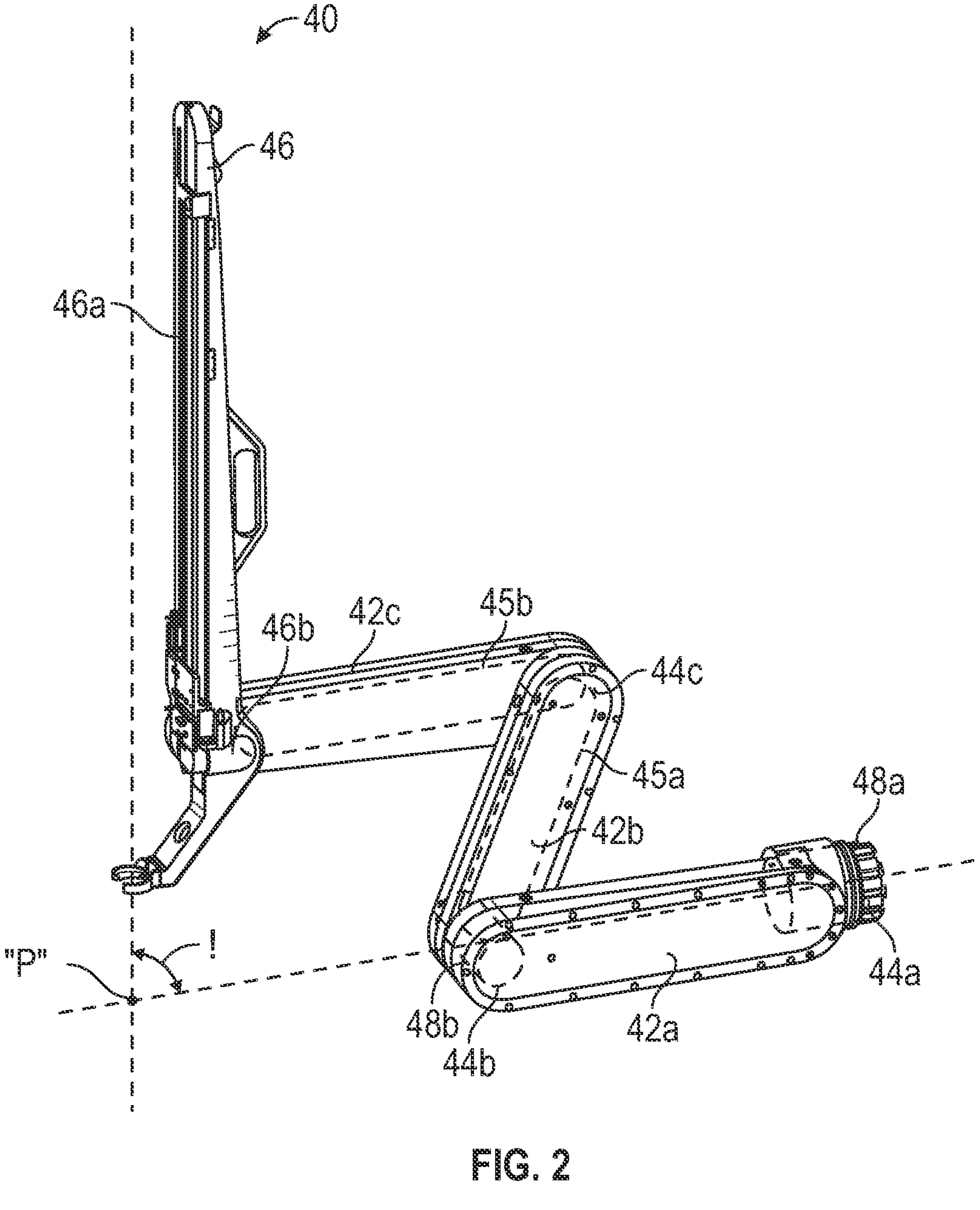
FIG. 2 is a perspective view of a surgical robotic arm of the surgical robotic system of FIG. 1 according to aspects of this disclosure.
Figure 3:
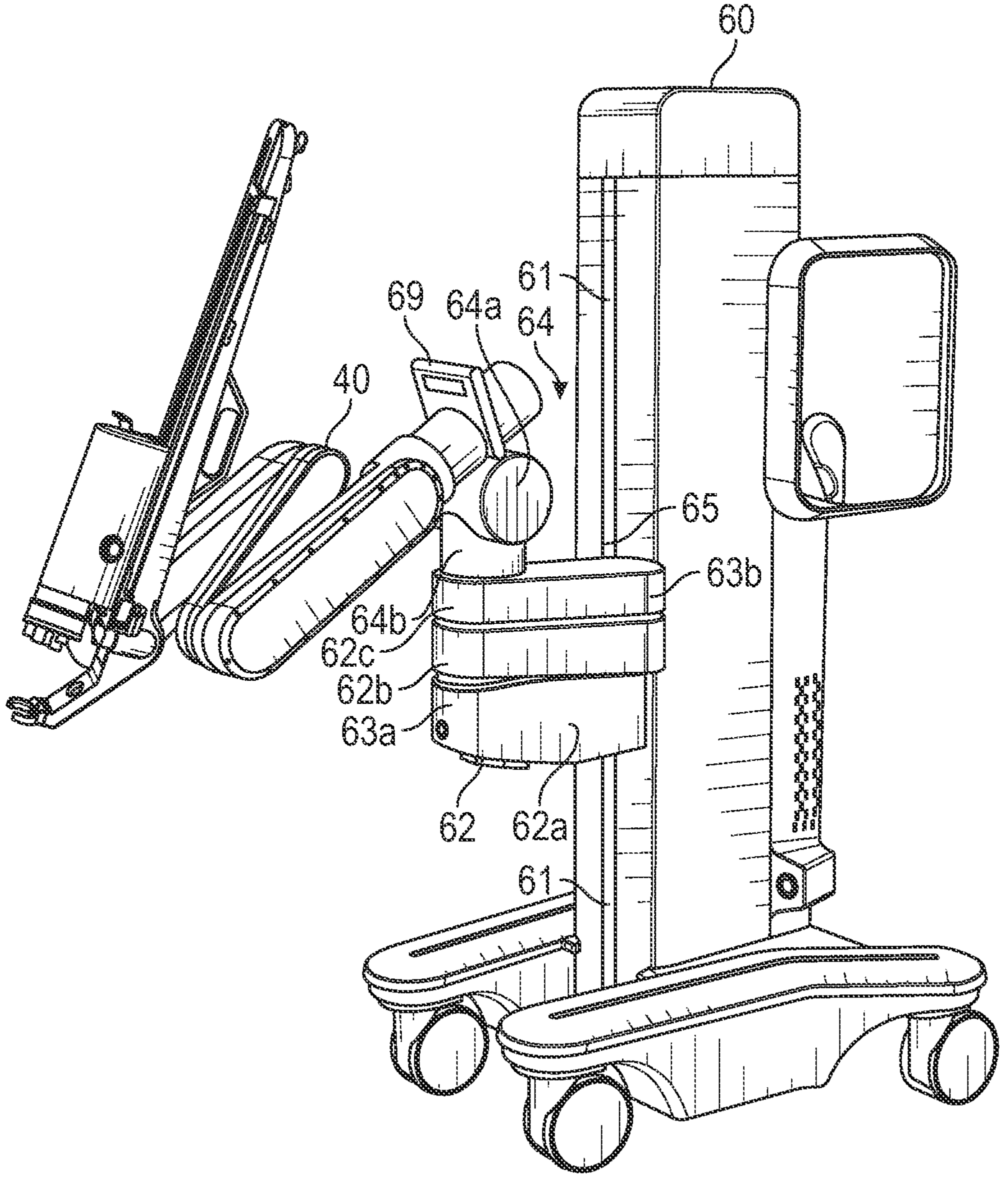
FIG. 3 is a perspective view of a setup arm with the surgical robotic arm of the surgical robotic system of FIG. 1 according to aspects of this disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

With reference again to FIG. 2, the robotic arm 40 also includes a holder 46 defining a second longitudinal axis and configured to receive an IDU 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector assembly 140) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*.

The robotic arm 40 also includes a plurality of manual override buttons 53 disposed on the IDU 52 and the setup arm 62. The clinician may press one or more of the buttons 53 to move the component associated with the button 53.

The joints 44*a* and 44*b* include actuators 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a remote center point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

Figure 4:
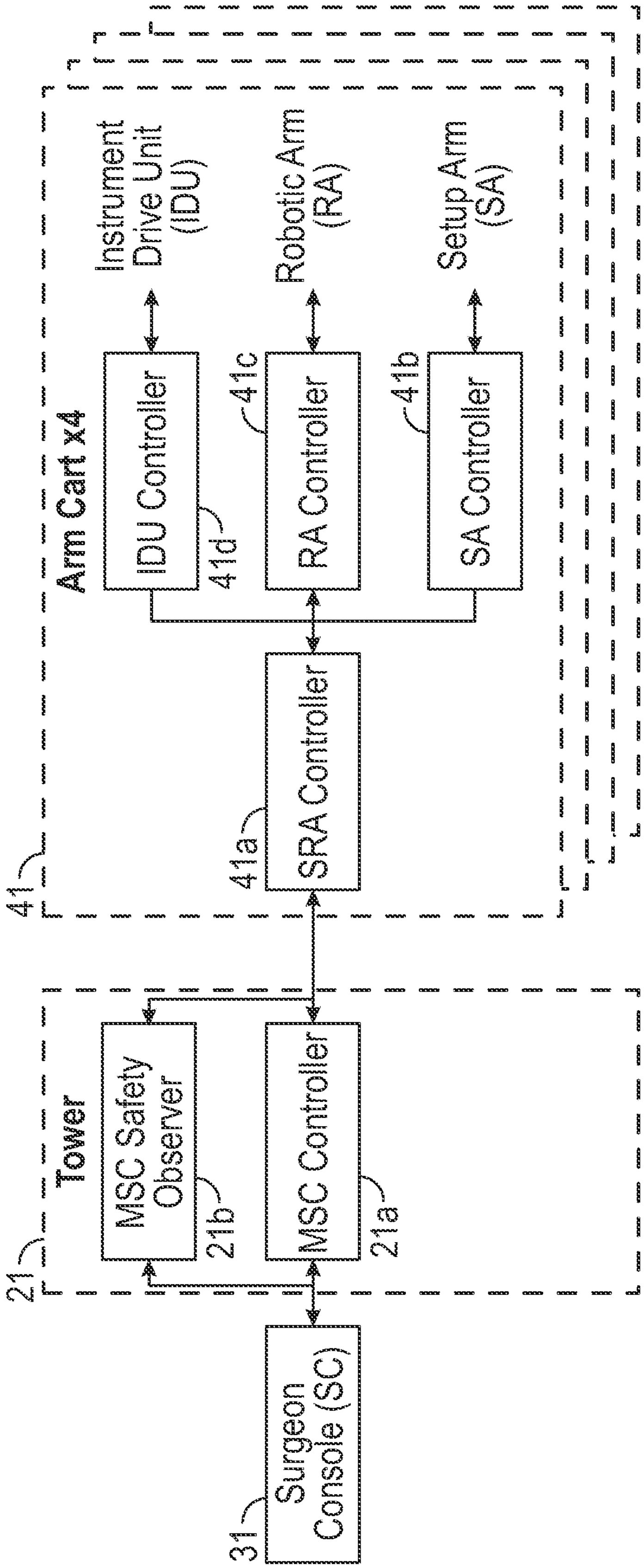
FIG. 4 is a schematic diagram of a computer architecture of the surgical robotic system of FIG. 1 according to aspects of this disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgical console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives back the actual joint angles and uses this information to determine force feedback commands that are transmitted back to the computer 31 of the surgical console 30 to provide haptic feedback through the handle controllers 38*a* and 38*b*. The handle controllers 38*a* and 38*b* include one or more haptic feedback vibratory devices that output haptic feedback. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

The setup arm controller 41*b* controls each of joints 63*a* and 63*b*, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled as follows. Initially, a pose of the handle controller controlling the robotic arm 40, e.g., the handle controller 38*a*, is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgical console 30. The desired pose of the surgical instrument 50 is relative to a fixed frame on the robotic arm 40. The pose of the handle controller 38*a* is then scaled by a scaling function executed by the controller 21*a*. In embodiments, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Turning to FIGS. 5A-7, a surgical instrument 110 provided in accordance with this disclosure generally includes a housing 120, a shaft 130 extending distally from housing 120, an end effector assembly 140 extending distally from shaft 130, and an actuation assembly 1100 disposed within housing 120 and operably associated with end effector assembly 140. Instrument 110 is detailed herein as an articulating electrosurgical forceps configured for use with a surgical robotic system, e.g., surgical robotic system 10 (FIG. 1). However, the aspects and features of instrument 110 provided in accordance with this disclosure, detailed below, are equally applicable for use with other suitable surgical instruments, e.g., graspers, staplers, clip appliers, and/or in other suitable surgical systems, e.g., motorized, other power-driven systems, and/or manually-actuated surgical systems (including handheld instruments).

Figure 5A:
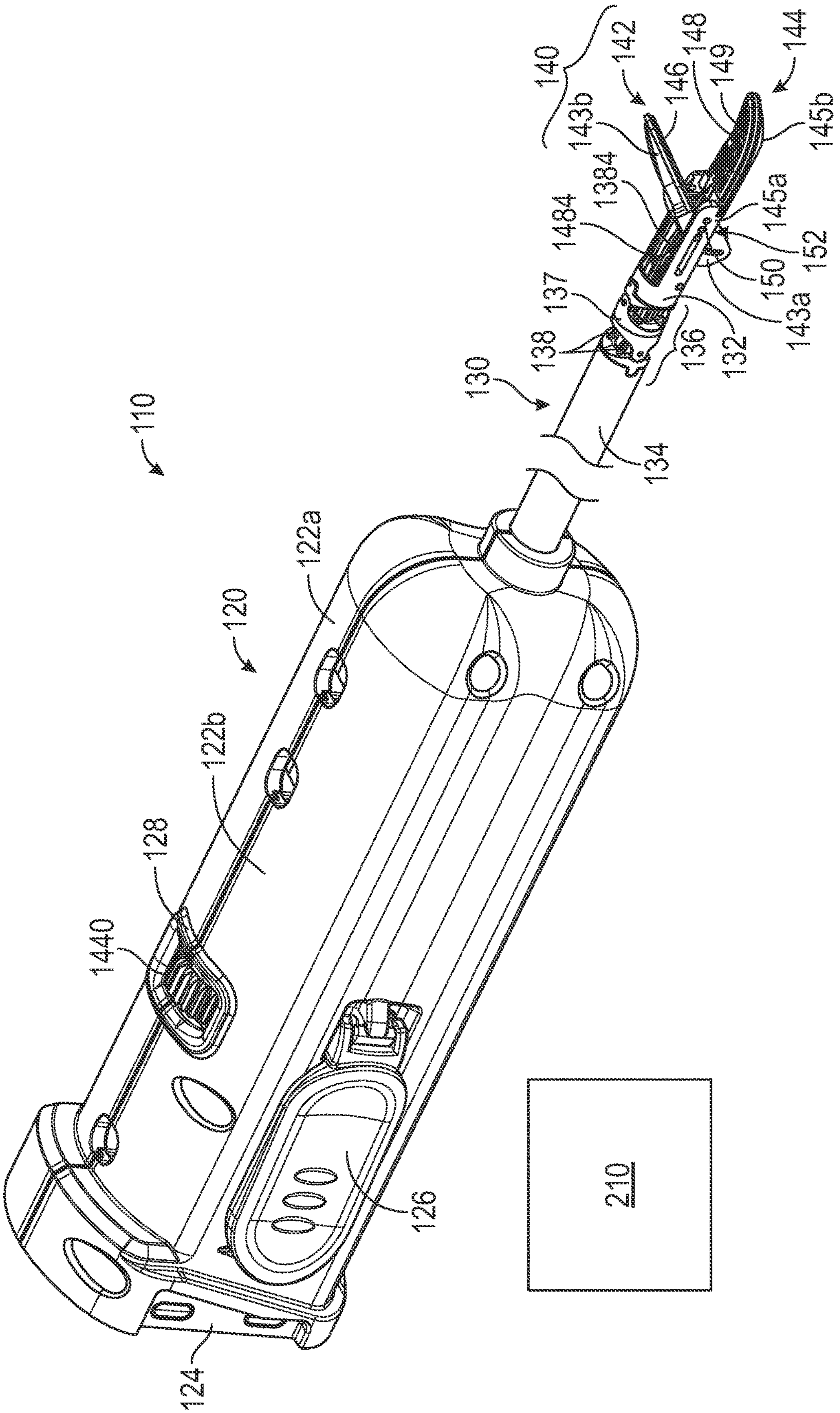
FIG. 5A is a perspective view of a surgical instrument provided in accordance with this disclosure configured for mounting on a robotic arm of a surgical robotic system such as the surgical robotic system of FIG. 1.

With particular reference to FIG. 5A, housing 120 of instrument 110 includes first and second body portion 122*a*, 122*b* and a proximal face plate 124 that cooperate to enclose actuation assembly 1100 therein. Proximal face plate 124 includes through-holes defined therein through which input couplers 1110-1140 (FIG. 6B) of actuation assembly 1100 extend. A pair of latch levers 126 (only one of which is illustrated in FIG. 5A) extending outwardly from opposing sides of housing 120 enable releasable engagement of housing 120 with a robotic arm of a surgical robotic system, e.g., surgical robotic system 10 (FIG. 1). A window 128 defined through housing 120 permits thumbwheel 1440 to extend therethrough to enable manual manipulation of thumbwheel 1440 from the exterior of housing 120 to permit manual opening and closing of end effector assembly 140.

Figure 6A:
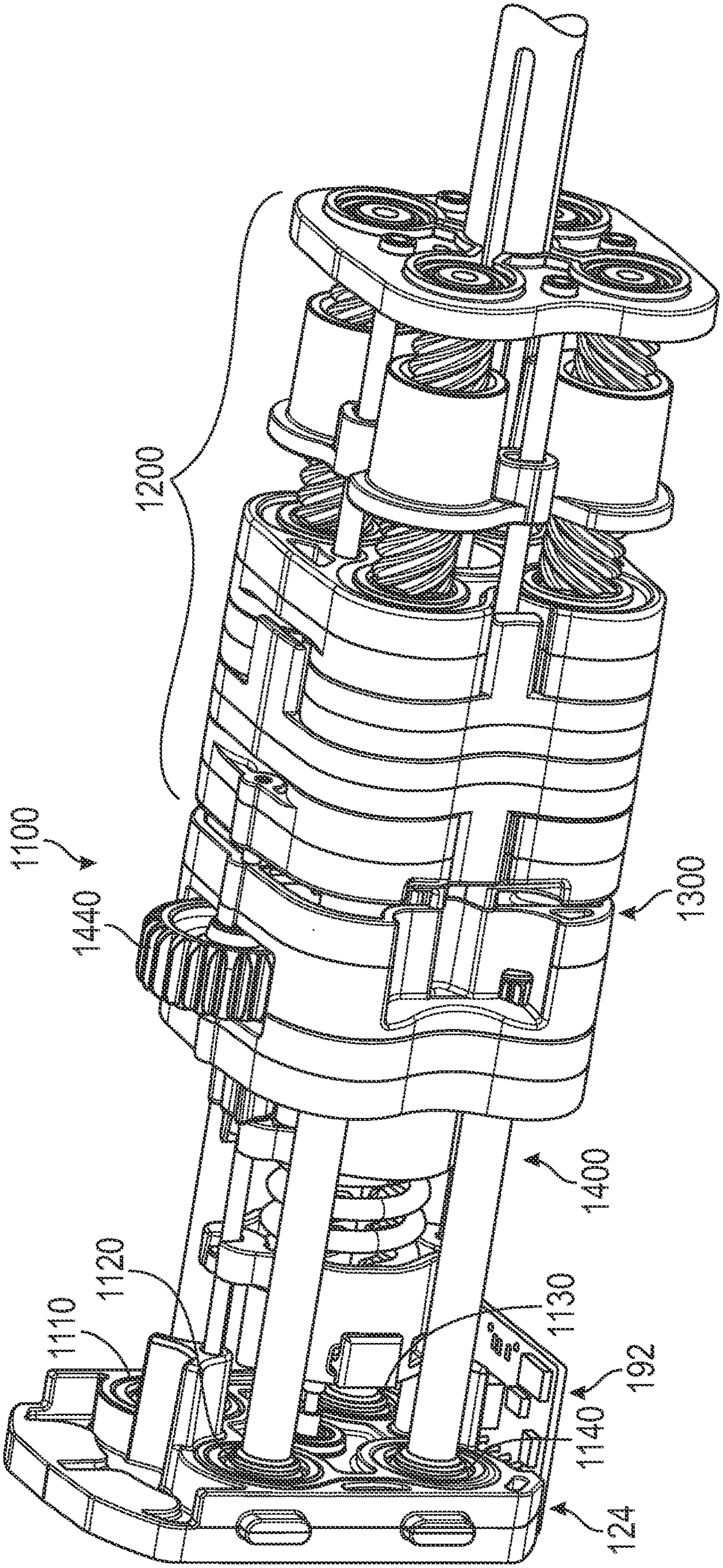
FIGS. 6A and 6B are front and rear perspective views, respectively, of a proximal portion of the surgical instrument of FIG. 5A, with an outer shell removed.
Figure 6B:
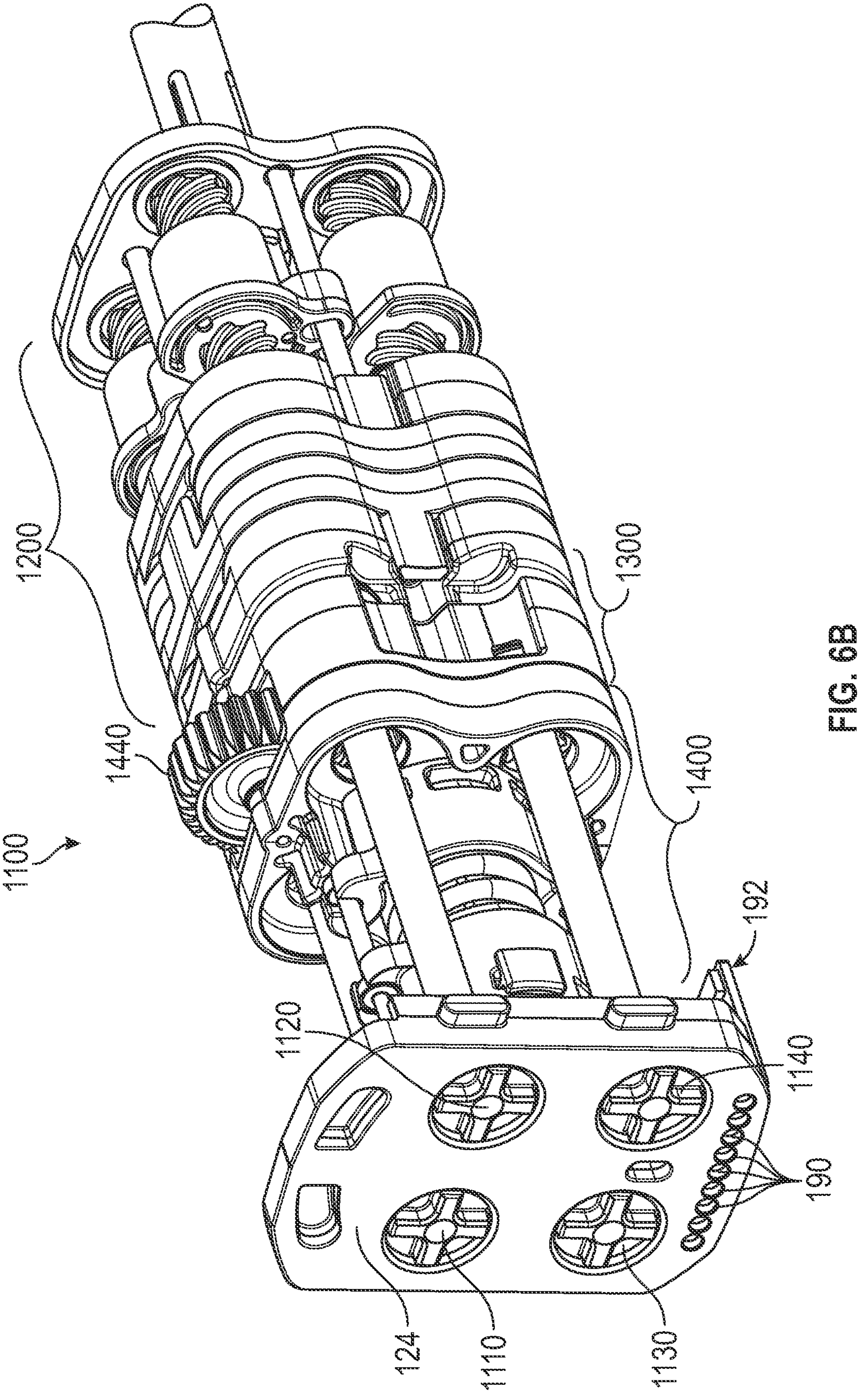
Figure 7:
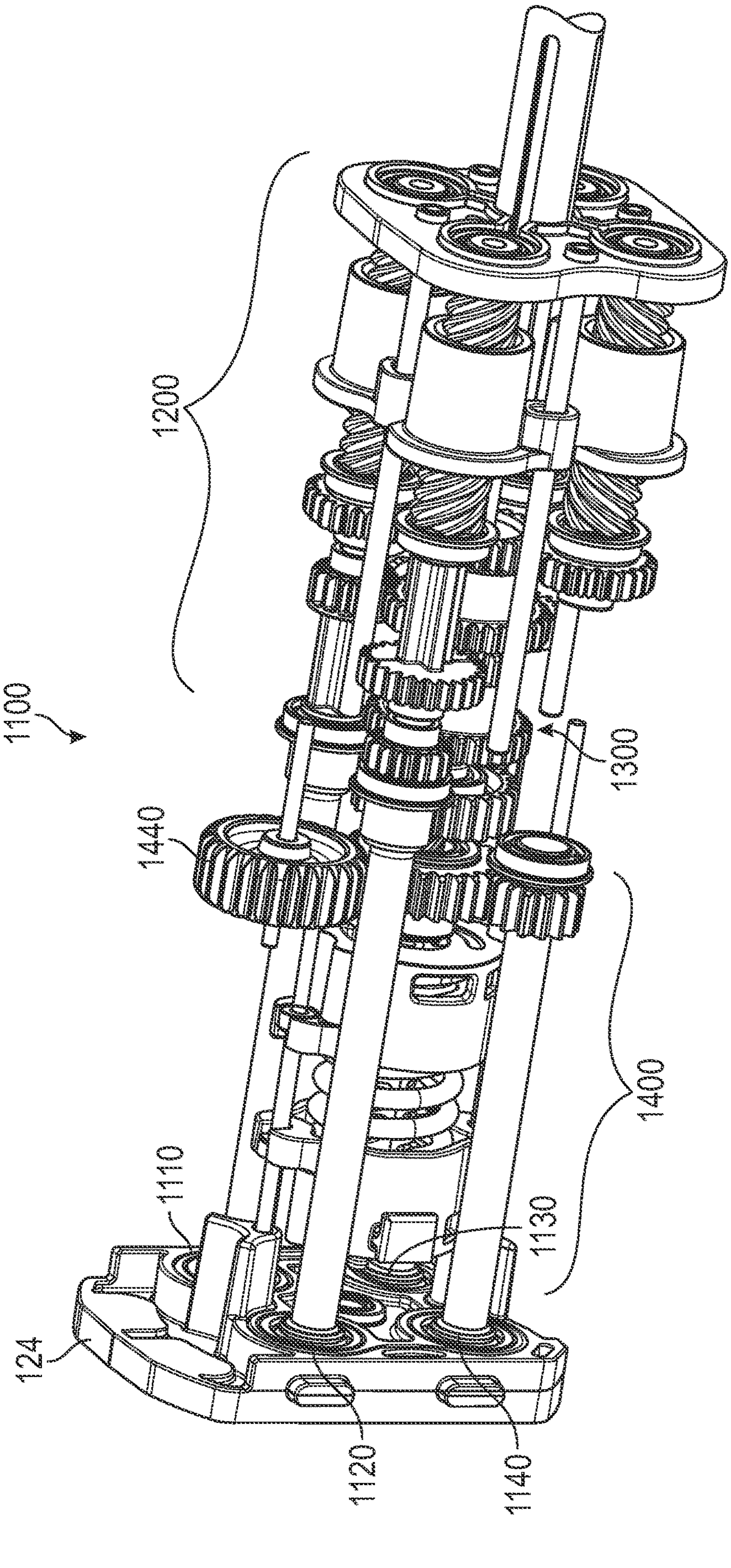
FIG. 7 is a front perspective view of the proximal portion of the surgical instrument of FIG. 5A with the outer shell and additional internal components removed.

Referring also to FIGS. 6A-7, a plurality of electrical contacts 190 extend through one or more apertures defined through proximal face plate 124 to enable electrical communication between instrument 110 and surgical robotic system 10 (FIG. 1) when instrument 110 is engaged on a robotic arm thereof, e.g., for the communication of data, control, and/or power signals therebetween. As an alternative to electrical contacts 190 extending through proximal face plate 124, other suitable transmitter, receiver, and/or transceiver components to enable the communication of data, control, and/or power signals are also contemplated, e.g., using RFID, Bluetooth®, WiFi®, or via any other suitable wired, wireless, contacted, or contactless communication method. At least some of the electrical contacts 190 are electrically coupled with electronics 192 mounted on an interior side of proximal face plate 124, e.g., within housing 120. Electronics 192 may include, for example, a storage device, a communications device (including suitable input/output components), and a CPU including a memory and a processor. Electronics 192 may be mounted on a circuit board or otherwise configured, e.g., as a chip.

The storage device of electronics 192 stores information relating to surgical instrument such as, for example: the item number, e.g., SKU number; date of manufacture; manufacture location, e.g., location code; serial number; lot number; use information; setting information; adjustment information; calibration information; security information, e.g., encryption key(s), and/or other suitable additional or alternative data. The storage device of electronics 192 may be, for example, a magnetic disk, flash memory, optical disk, or other suitable data storage device.

As an alternative or in addition to storing the above-noted information in the storage device of electronics 192, some or all of such information, e.g., the use information, calibration information, setting information, and/or adjustment information, may be stored in a storage device associated with surgical robotic system 10 (FIG. 1), a remote server, a cloud server, etc., and accessible via instrument 110 and/or surgical robotic system 10 (FIG. 1). In such configurations, the information may, for example, be updated by manufacturer-provided updates, and/or may be applied to individual instruments, units of instruments (e.g., units from the same manufacturing location, manufacturing period, lot number, etc.), or across all instruments. Further still, even where the information is stored locally on each instrument, this information may be updated by manufacturer-provided updates manually or automatically upon connection to the surgical robotic system 10 (FIG. 1).

Referring again to FIG. 5A, shaft 130 of instrument 110 includes a distal segment 132, a proximal segment 134, and an articulating section 136 disposed between the distal and proximal segments 132, 134, respectively. Articulating section 136 includes one or more articulating components 137, e.g., links, joints, etc. A plurality of articulation cables 138, e.g., four (4) articulation cables, or other suitable actuators, extend through articulating section 136. More specifically, articulation cables 138 are operably coupled to distal segment 132 of shaft 130 at the distal ends thereof and extend proximally from distal segment 132 of shaft 130, through articulating section 136 of shaft 130 and proximal segment 134 of shaft 130, and into housing 120, wherein articulation cables 138 operably couple with an articulation sub-assembly 1200 of actuation assembly 1100 (FIG. 6A) to enable selective articulation of distal segment 132 (and, thus end effector assembly 140) relative to proximal segment 134 and housing 120, e.g., about at least two axes of articulation (yaw and pitch articulation, for example). Articulation cables 138 are arranged in a generally rectangular configuration, although other suitable configurations are also contemplated. In some configurations, as an alternative, shaft 130 is substantially rigid, malleable, or flexible and not configured for active articulation. Articulation sub-assembly 1200 is described in greater detail below.

With respect to articulation of end effector assembly 140 relative to proximal segment 134 of shaft 130, actuation of articulation cables 138 may be accomplished in pairs. More specifically, in order to pitch end effector assembly 140, the upper pair of cables 138 are actuated in a similar manner while the lower pair of cables 138 are actuated in a similar manner relative to one another but an opposite manner relative to the upper pair of cables 138. With respect to yaw articulation, the right pair of cables 138 are actuated in a similar manner while the left pair of cables 138 are actuated in a similar manner relative to one another but an opposite manner relative to the right pair of cables 138. Other configurations of articulation cables 138 or other articulation actuators are also contemplated.

Continuing with reference to FIG. 5A, end effector assembly 140 includes first and second jaw members 142, 144, respectively. Each jaw member 142, 144 includes a proximal flange portion 143*a*, 145*a* and a distal body portion 143*b*, 145*b*, respectively. Distal body portions 143*b*, 145*b* define opposed tissue-contacting surfaces 146, 148, respectively. Proximal flange portions 143*a*, 145*a* are pivotably coupled to one another about a pivot 150 and are operably coupled to one another via a cam-slot assembly 152 including a cam pin slidably received within cam slots defined within the proximal flange portion 143*a*, 145*a* of at least one of the jaw members 142, 144, respectively, to enable pivoting of jaw member 142 relative to jaw member 144 and distal segment 132 of shaft 130 between a spaced-apart position (e.g., an open position of end effector assembly 140) and an approximated position (e.g., a closed position of end effector assembly 140) for grasping tissue between tissue-contacting surfaces 146, 148. As an alternative to this unilateral configuration, a bilateral configuration may be provided whereby both jaw members 142, 144 are pivotable relative to one another and distal segment 132 of shaft 130. Other suitable jaw actuation mechanisms are also contemplated.

In configurations, a longitudinally-extending knife channel 149 (only knife channel 149 of jaw member 144 is illustrated; the knife channel of jaw member 142 is similarly configured) is defined through the tissue-contacting surface 146, 148 of one or both jaw members 142, 144. In such aspects, a knife assembly including a knife rod 1384 extending from housing 120 through shaft 130 to end effector assembly 140 and a knife blade 147 fixed to or otherwise coupled to a distal end of the knife rod 1384. Knife blade 147 is disposed within end effector assembly 140 and is selectively translatable through the knife channel(s) 149 and between the jaw member 142, 144 to cut tissue grasped between tissue-contacting surfaces 146, 148 of jaw members 142, 144, respectively. Knife rod 1384 is operably coupled to a knife drive sub-assembly 1300 (FIG. 7) of actuation assembly 1100 (FIGS. 6A-6B) at a proximal end thereof to enable the selective actuation of the knife rod 1384 to, in turn, reciprocate knife blade 147 between jaw members 142, 144 to cut tissue grasped between tissue-contacting surfaces 146, 148. As an alternative to a longitudinally-advanceable mechanical knife, other suitable mechanical cutters are also contemplated, e.g., guillotine-style cutters, as are energy-based cutters, e.g., RF electrical cutters, ultrasonic cutters, etc., in static or dynamic configurations.

Tissue-contacting surfaces 146, 148 of jaw members 142, 144, respectively, are at least partially formed from an electrically conductive material and are energizable to different potentials to enable the conduction of RF electrical energy through tissue grasped therebetween, although tissue-contacting surfaces 146, 148 may alternatively be configured to supply any suitable energy, e.g., thermal, microwave, light, ultrasonic, ultrasound, etc., through tissue grasped therebetween for energy-based tissue treatment. Instrument 110 defines a conductive pathway (not shown) through housing 120 and shaft 130 to end effector assembly 140 that may include lead wires, contacts, and/or electrically-conductive components to enable electrical connection of tissue-contacting surfaces 146, 148 of jaw members 142, 144, respectively, to an energy source 200, e.g., an electrosurgical generator, for supplying energy to tissue-contacting surfaces 146, 148 to treat, e.g., seal, tissue grasped between tissue-contacting surfaces 146, 148.

Referring still to FIG. 5A, a drive rod 1484 is operably coupled to cam-slot assembly 152 of end effector assembly 140, e.g., engaged with the cam pin thereof, such that longitudinal actuation of drive rod 1484 pivots jaw member 142 relative to jaw member 144 between the spaced-apart and approximated positions. More specifically, urging drive rod 1484 proximally pivots jaw member 142 relative to jaw member 144 towards the approximated position while urging drive rod 1484 distally pivots jaw member 142 relative to jaw member 144 towards the spaced-apart position. However, other suitable mechanisms and/or configurations for pivoting jaw member 142 relative to jaw member 144 between the spaced-apart and approximated positions in response to selective actuation of drive rod 1484 are also contemplated. Drive rod 1484 extends proximally from end effector assembly 140 through shaft 130 and into housing 120 wherein drive rod 1484 is operably coupled with a jaw drive sub-assembly 1400 of actuation assembly 1100 (FIGS. 6A-6B) to enable selective actuation of end effector assembly 140 to grasp tissue therebetween and apply a jaw force within an appropriate jaw force range.

In some aspects of this disclosure, control of various controllable features of surgical instrument 110 may be mapped to one or more foot pedals 36 of surgical console 30. The controllable features of surgical instrument 110 may include, but are not limited to, actuation of drive rod 1484 to pivot jaw member 142 toward jaw member 144 to grasp tissue between tissue-contacting surfaces 146, 148; delivery of electrosurgical energy to tissue-contacting surfaces 146, 148 for sealing tissue grasped therebetween; actuation of knife rod 1384 to extend knife blade 147 through jaw members 142, 144 to cut tissue grasped between tissue-contacting surfaces 146, 148; actuation of knife rod 1384 to retract knife blade 147 through jaw members 142, 144 after tissue grasped between tissue-contacting surfaces 146, 148 is cut; and actuation of drive rod 1484 to pivot jaw member 142 away from jaw member 144 to release grasped tissue. Energy source 200 may be configured to communicate with various components of surgical robotic system 10 such that user input received at surgical console 30 (e.g., the mode of operation of surgical instrument 110, actuation/control of the aforementioned controllable features of surgical instrument 110, etc.) may be ascertained by energy source 200.

In some aspects of the disclosure, each of the aforementioned controllable features of instrument 110 may be individually controlled by actuation of one of foot pedals 36 of surgical console 30. For example, each controllable feature of surgical instrument 110 may be controlled by its own designated foot pedal, by separate and distinct actuations of the same foot pedal, or by separate and distinct actuations of one or more foot pedals.

In one embodiment of this disclosure, handle controllers 38*a* and 38*b* (or optionally one of foot pedals 36) may be actuated to cause actuation of drive rod 1484 to pivot jaw member 142 toward jaw member 144 to grasp tissue between tissue-contacting surfaces 146, 148. With tissue grasped between tissue-contacting surfaces 146, 148, actuation of one of foot pedals 36 may cause delivery of electrosurgical energy to tissue-contacting surfaces 146, 148 for sealing tissue grasped therebetween. In some aspects, actuation of the foot pedal may include maintaining the foot pedal in an actuated position (e.g., by a user pressing and holding down the foot pedal in an actuated position) until the tissue sealing cycle is complete. For example, in response to an indication (e.g., generated by the energy source 200) that a tissue sealing cycle is complete, a clinician at surgical console 30 may release the actuated foot pedal to terminate a demand for the energy source 200 to deliver energy to the tissue-contacting surfaces 146, 148. The indication will be suitable to alert the clinician that the tissue sealing cycle is complete. Examples of such an indication include, but are not limited to, an audible tone, a visual graphic (e.g. displayed on a display screen of energy source 200), or the like. In aspects of this disclosure, energy source 200 will automatically terminate delivery of energy to tissue-contacting surfaces 146, 148 at the conclusion of a tissue sealing cycle, as determined by the energy source 200, regardless of whether the foot pedal at the surgical console 30 is actuated or unactuated. As described above, if certain criteria have been satisfied indicating that the tissue sealing cycle is complete and that it is safe to cut the sealed tissue, the user flow for the clinician may be sped up by requiring only a single actuation of a foot pedal (e.g., a "single-tap") to effect a tissue cut following the completion of a tissue sealing cycle. In aspects of this disclosure, the single-tap criteria includes: i) a determination that the tissue sealing cycle is complete; ii) maintaining of end effector assembly 140 in the closed position and grasping the tissue that has been sealed; and iii) receiving a single actuation or "single-tap" of a foot pedal within a predetermined period of time following the actuation of one of foot pedals 36 to start the tissue sealing cycle. In some embodiments, the predetermined period of time may be initiated upon completion of the tissue sealing cycle. In aspects of this disclosure, the predetermined period of time may be less than about 15 seconds. In other aspects of this disclosure, the predetermined period of time may be less than about 10 seconds. In aspects of this disclosure, the predetermined period of time may be between about 0.75 seconds and about 15 seconds. In other aspects of this disclosure, the predetermined period of time may be between about 0.5 seconds and about 15 seconds. In aspects of this disclosure, the predetermined period of time may be between about 0.5 seconds and about 10 seconds. In other aspects of this disclosure, the predetermined period of time may be between about 0.75 seconds and about 10 seconds. Once the tissue sealing cycle is complete and the clinician at surgical console 30 releases the foot pedal, if end effector assembly 140 remains in the closed position to grasp the sealed tissue (or has otherwise not moved toward the open position) and the clinician actuates a foot pedal with a single-tap (e.g., using the same foot pedal that was actuated to effect the tissue sealing cycle or using a different foot pedal) within the predetermined period of time, the knife rod 1384 is actuated to reciprocate knife blade 147 and cut the sealed tissue. As indicated above, in some embodiments of this disclosure, the aforementioned single-tap of the foot pedal to effect cutting of the sealed tissue may be replaced by a single actuation of a different actuation device of the disclosed surgical system such as, for example, a handle controller (e.g., handle controllers 38*a*, 38*b*), a hand controller button, a paddle controller, a GUI controller (e.g., via display 34 or display 23), voice activation, or any suitable actuation device configured to help decrease procedure time and/or improve the user flow.

In aspects of this disclosure, a determination of whether end effector 140 is or remains in the closed position with respect to the aforementioned single-tap criteria may be based on a determined position of drive rod 1484. For example, a relatively proximal longitudinal position of drive rod 1484 may indicate jaw members 142, 144 are in the approximated position (corresponding to the closed position of end effector 140) while a relatively distal longitudinal position of drive rod 1484 may indicate jaw members 142, 144 are in or moved toward the spaced-apart position (corresponding to the open position of end effector 140).

If the clinician does not single-tap the foot pedal within the predetermined period of time and/or end effector assembly 140 moves toward the open position, a single-tap of a foot pedal will not cause actuation of knife rod 1384 to reciprocate knife blade 147 to cut the tissue. If the clinician desires to cut tissue outside of the aforementioned single-tap criteria being satisfied, the clinician in this scenario must instead double-tap a foot pedal to cause actuation of knife rod 1384 to reciprocate knife blade 147 to cut the tissue. In aspects of the disclosure, a determination that the tissue is not sealed may cause surgical robotic system 10 to deviate from the workflow, for example, by re-initiating tissue sealing.

In some aspects of the disclosure, each of the aforementioned controllable features of instrument 110 may be controlled by actuation of one of foot pedals 36 of surgical console 30 individually when surgical instrument 110 is operated in the manual mode. For example, each controllable feature of instrument 110 may be controlled by its own designated foot pedal, by separate and distinct actuations of the same foot pedal, or by separate and distinct actuations of one or more foot pedals.

In other aspects of the disclosure, more than one of the aforementioned controllable features of surgical instrument 110 may be controlled by the same foot pedal and/or by a single actuation of the same foot pedal when surgical instrument 110 is operated in the auto-cut mode. In one example of operation in the auto-cut mode, a single foot pedal may be actuated once and maintained as actuated to control any one or more of the aforementioned controllable features of surgical instrument 110. In this instance, a first controllable feature of surgical instrument 110 may be controlled in response to actuation of the foot pedal and, in response to the foot pedal being maintained as actuated, one or more additional controllable features of surgical instrument 110 may be controlled based on feedback provided to robotic system 10. The feedback provided to robotic system 10 may be in response to execution of a procedure associated with the first controllable feature of surgical instrument 110 (e.g., delivery of electrosurgical energy to tissue-contacting surfaces 146, 148 for sealing tissue grasped therebetween). Based on that feedback, an additional procedure associated with an additional controllable feature of surgical instrument 110 (e.g., actuation of knife rod 1384 to extend knife blade 147 through jaw members 142, 144 to cut tissue grasped between tissue-contacting surfaces 146, 148) may be or may not be executed in response to the foot pedal being maintained as actuated. In contrast, a single actuation of the foot pedal during operation in the manual mode controls a single controllable feature of surgical instrument 110 and so maintaining the foot pedal as actuated does not cause other controllable features of surgical instrument 110 to be controlled and/or procedures associated with other controllable features of surgical instrument 110 to be executed. Thus, in the manual mode of operation, reliance on feedback provided to robotic system 10 may not be necessary since the controllable features of surgical instrument 110 are controlled by separate and distinct actuations of the foot pedal or separate and distinct actuations of one or more foot pedals.

In another embodiment of this disclosure, handle controllers 38*a* and 38*b* (or optionally one of foot pedals 36) may be actuated to cause actuation of drive rod 1484 to pivot jaw member 142 toward jaw member 144 to grasp tissue between tissue-contacting surfaces 146, 148. With tissue grasped between tissue-contacting surfaces 146, 148 and the auto-cut mode of operation selected, actuation of one of foot pedals 36 may cause delivery of electrosurgical energy to tissue-contacting surfaces 146, 148 for sealing tissue grasped therebetween and actuation of knife rod 1384 to reciprocate knife blade 147 to cut the sealed tissue (e.g., upon indication that the tissue is sealed). Thus, a user may actuate a single foot pedal once to cause tissue-contacting surfaces 146, 148 to seal grasped tissue and knife blade 147 to cut the sealed tissue. In some aspects, actuation of the foot pedal may include maintaining the foot pedal in an actuated position (e.g., by a user pressing and holding down the foot pedal in an actuated position) until the tissue sealing and tissue cutting cycles are completed and/or indicated as completed by the energy source 200 and/or the surgical robotic system 10. As detailed below, properties (e.g., impedance and/or temperature) of tissue grasped between jaw members 142, 144 during the tissue sealing process may be monitored for determining when tissue sealing has been completed (e.g., when an effective tissue seal has been achieved). With respect to the above-described embodiment, reciprocation of knife blade 147 to cut tissue is based on a determination that the tissue is sealed. When it is determined that the tissue is not sealed, the knife rod 1384 is not actuated to reciprocate knife blade 147 to cut the tissue. In this scenario, a single actuation of the foot pedal and/or maintaining the foot pedal in an actuated position will not cause the knife blade 147 to cut the tissue. In aspects of the disclosure, a determination that the tissue is not sealed may cause surgical robotic system 10 to deviate from the auto-cut mode workflow, for example, by deactivating auto-cut mode and activating the manual mode of operation to enable the user to manually control tissue sealing and tissue cutting (e.g., via actuation of the foot pedal). In other aspects, surgical robotic system 10 may deactivate and restart auto-cut mode to re-initiate tissue sealing. In aspects of the disclosure, deactivation of auto-cut mode and/or activation of manual mode may be effected either manually by the user or automatically by surgical robotic system 10 in response to a determination that the tissue is not sealed.

In still yet other aspects of this disclosure, maintaining the foot pedal in the actuated position may additionally cause actuation of drive rod 1484 to pivot jaw member 142 away from jaw member 144 to release tissue from between tissue-contacting surfaces 146, 148 after the tissue is cut by knife blade 147. In this instance, a single actuation of the same foot pedal may cause sealing of tissue grasped between tissue-contacting surfaces 146, 148, cutting of the sealed tissue, and movement of jaw members 142, 144 from the approximated position to the spaced-apart position to release the cut tissue from between tissue-contacting surfaces 146, 148. If knife blade 147 fails to properly actuate (e.g., reciprocate, advance, retract, etc.) to cut the sealed tissue, jaw members 142, 144 may be maintained in the approximated position to continue grasping the uncut sealed tissue until knife blade 147 is properly reciprocated. In some aspects of the disclosure, failure of knife blade 147 to properly actuate to cut tissue may cause surgical robotic system 10 to deviate from the auto-cut mode workflow similarly as described above with respect to a determination that the tissue is not sealed.

Figure 5B:
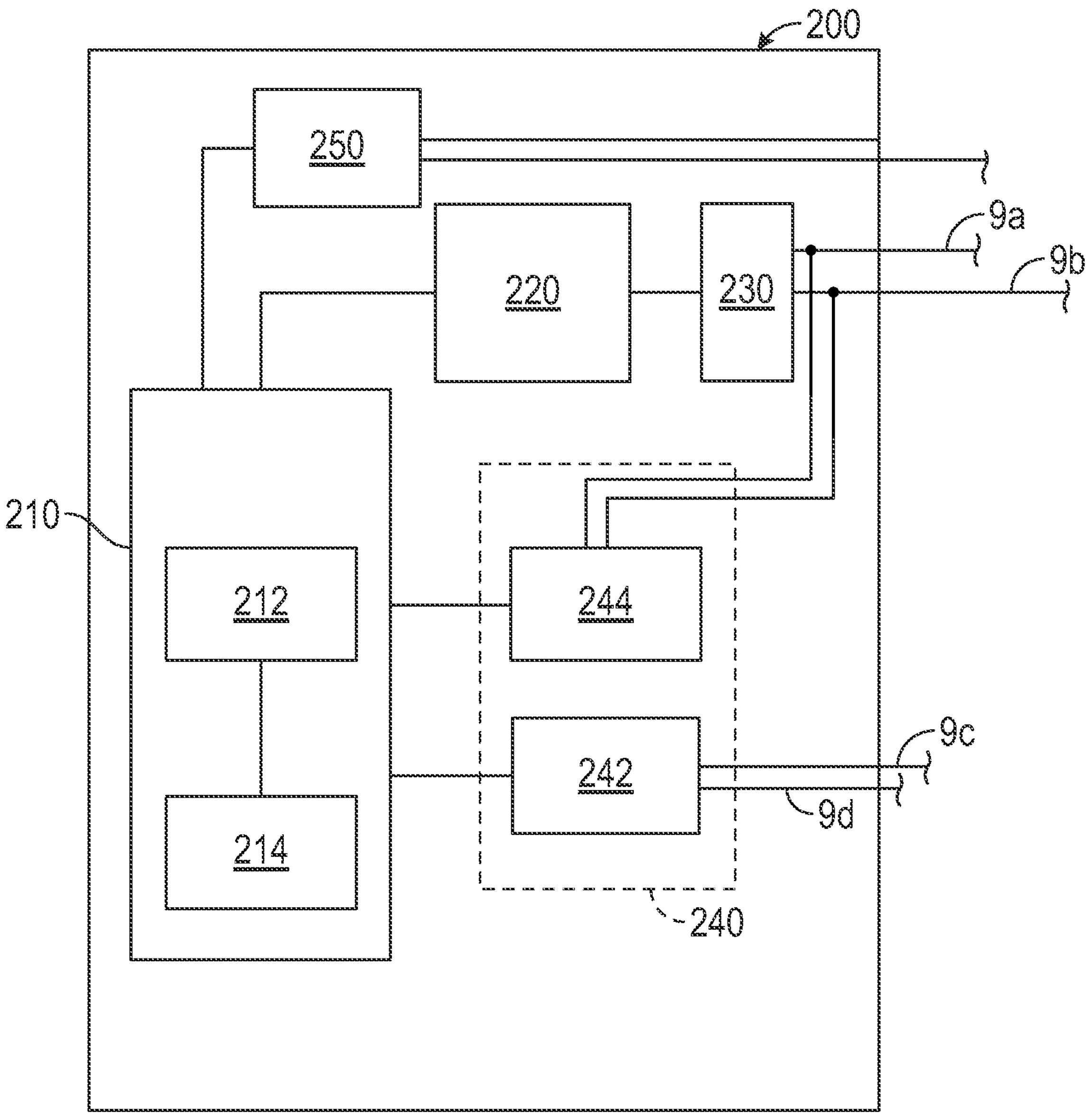
FIG. 5B is a is a schematic illustration of an energy source provided in accordance with this disclosure and configured for use with the surgical instrument of FIG. 5A and a surgical robotic system such as the surgical robotic system of FIG. 1.

With reference to FIG. 5B, energy source 200 is described for use with surgical instrument 110 as part of surgical robotic system 10. However, energy source 200 may also be configured for use with any other suitable surgical instrument, such as the various embodiments of surgical instruments 50 provided herein. Energy source 200 is configured to both supply and control the supply of energy to end effector assembly 140 for sealing tissue, and/or to communicate with surgical robotic system 10 for manipulating end effector assembly 140, e.g., opening and closing jaw members 142, 144. In particular, in the manual mode, energy source 200 provides feedback with respect to the configuration of end effector assembly 140 and the tissue sealing process while, in the auto-cut mode, energy source 200 in conjunction with surgical robotic system 10 operates surgical instrument 110 for grasping, sealing, and/or cutting tissue, via feedback-based control.

Energy source 200 includes a controller 210, a high voltage DC power supply 220 (or other suitable power supply), an RF output stage 230 (or other suitable output depending on the energy delivered to end effector assembly 100), a sensor module 840, and a motor output module 250. Energy source 200 may further include various input controls, e.g., buttons, activators, switches, touch screens, etc., for controlling energy source 200. In addition, energy source 200 may include one or more display screens for providing a variety of output information, e.g., intensity settings, treatment complete indicators, etc.

Controller 210 includes a processor 212 connected to a computer-readable storage medium or memory 214, which may be a volatile-type memory, e.g., RAM, or a non-volatile type memory, e.g., flash media, disk media, etc. Controller 210 is coupled to power supply 220, RF output stage 230, and motor output module 250, thus allowing processor 212 to control the output of energy source 200. In particular, power supply 220 and RF output stage 230, based on control signals received from processor 212 and/or user input at energy source 200 and/or surgical console 30, cooperate to selectively provide energy to tissue-contacting surfaces 146, 148, via wires 9*a* and 9*b* to seal tissue. Motor output module 250, on the other hand, provides control signals to surgical robotic system 10 for controlling end effector assembly 140, e.g., opening and closing jaw members 142, 144 and/or translating knife blade 147. Processor 212 is further coupled to sensor module 240 for receiving feedback signals from sensor module 240 to perform feedback-based control of end effector assembly 140. Memory 214 may store suitable instructions for indicating the sequence, duration, and/or parameters of the various actions controlled via controller 210. Feedback received by controller 210 from sensor module 240 and/or user input received at energy source 200 may be communicated by controller 210 to surgical robotic system 10.

Sensor module 240 includes a tissue presence unit 242 and a tissue property unit 244, although sensor module 240 may further include a plurality of other sensor units for measuring and providing feedback with respect to a variety of mechanical, tissue, and/or energy properties. Tissue presence unit 242 is coupled to suitable sensors (not shown) on end effector assembly 140 via wires 9*c* and 9*d* and is configured to receive signals therefrom for determining the presence of tissue and/or the positioning of tissue disposed between jaw members 142, 144 when jaw members 142, 144 are disposed in the spaced-apart position, and for providing the same to controller 210. Tissue property unit 244 is coupled to wires 9*a* and 9*b* for sensing one or more properties of tissue grasped between jaw members 142, 144 during tissue sealing and/or tissue cutting and for providing the same to controller 210. In particular, tissue property unit 244 may be configured to sense the impedance of tissue (in addition to other properties such as temperature) grasped between jaw members 142, 144 during the conduction of energy between tissue-contacting surfaces 146, 148 and through tissue to monitor the tissue sealing process for determining when tissue sealing has been completed and/or determining whether tissue is sufficiently sealed. Tissue property unit 244, provides the above-noted impedance (or other) data to controller 210.

As an alternative to energy source 200, surgical instrument 110 may include an onboard controller, motor output module, and sensor module that operate similar to the corresponding components of energy source 200. In such an embodiment, surgical instrument 110 need only be coupled to a generic energy supply that provides energy to end effector assembly 140 for sealing tissue, while all the feedback based control of surgical instrument 110 in the auto-cut mode of operation is effected via the onboard components of surgical instrument 110.

With additional reference to FIGS. 6A-7, as noted above, actuation assembly 1100 is disposed within housing 120 and includes an articulation sub-assembly 1200, a knife drive sub-assembly 1300, and a jaw drive sub-assembly 1400. Articulation sub-assembly 1200 is operably coupled between first and second input couplers 1110, 1120, respectively, of actuation assembly 1100 and articulation cables 138 (FIG. 5A) such that, upon receipt of appropriate inputs into first and/or second input couplers 1110, 1120, articulation sub-assembly 1200 manipulates cables 138 (FIG. 5A) to articulate end effector assembly 140 in a desired direction, e.g., to pitch and/or yaw end effector assembly 140. Articulation sub-assembly 1200 is described in greater detail below.

Knife drive sub-assembly 1300 is operably coupled between third input coupler 1130 of actuation assembly 1100 and the knife rod 1384 such that, upon receipt of appropriate input into third input coupler 1130, knife drive sub-assembly 1300 manipulates the knife rod 1384 to reciprocate the knife blade 147 between jaw members 142, 144 to cut tissue grasped between tissue-contacting surfaces 146, 148.

Jaw drive sub-assembly 1400 is operably coupled between fourth input coupler 1140 of actuation assembly 1100 and drive rod 1484 such that, upon receipt of appropriate input into fourth input coupler 1140, jaw drive sub-assembly 1400 pivots jaw members 142, 144 between the spaced-apart and approximated positions to grasp tissue therebetween and apply a jaw force within an appropriate jaw force range.

Actuation assembly 1100 is configured to operably interface with a surgical robotic system, e.g., system 10 (FIG. 1), when instrument 110 is mounted on a robotic arm thereof, to enable robotic operation of actuation assembly 1100 to provide the above-detailed functionality. That is, surgical robotic system 10 (FIG. 1) selectively provides inputs, e.g., rotational inputs to input couplers 1110-1140 of actuation assembly 1100 to articulate end effector assembly 140, grasp tissue between jaw members 142, 144, and/or cut tissue grasped between jaw members 142, 144. However, as noted above, it is also contemplated that actuation assembly 1100 be configured to interface with any other suitable surgical systems, e.g., a manual surgical handle, a powered surgical handle, etc.

Figure 8:
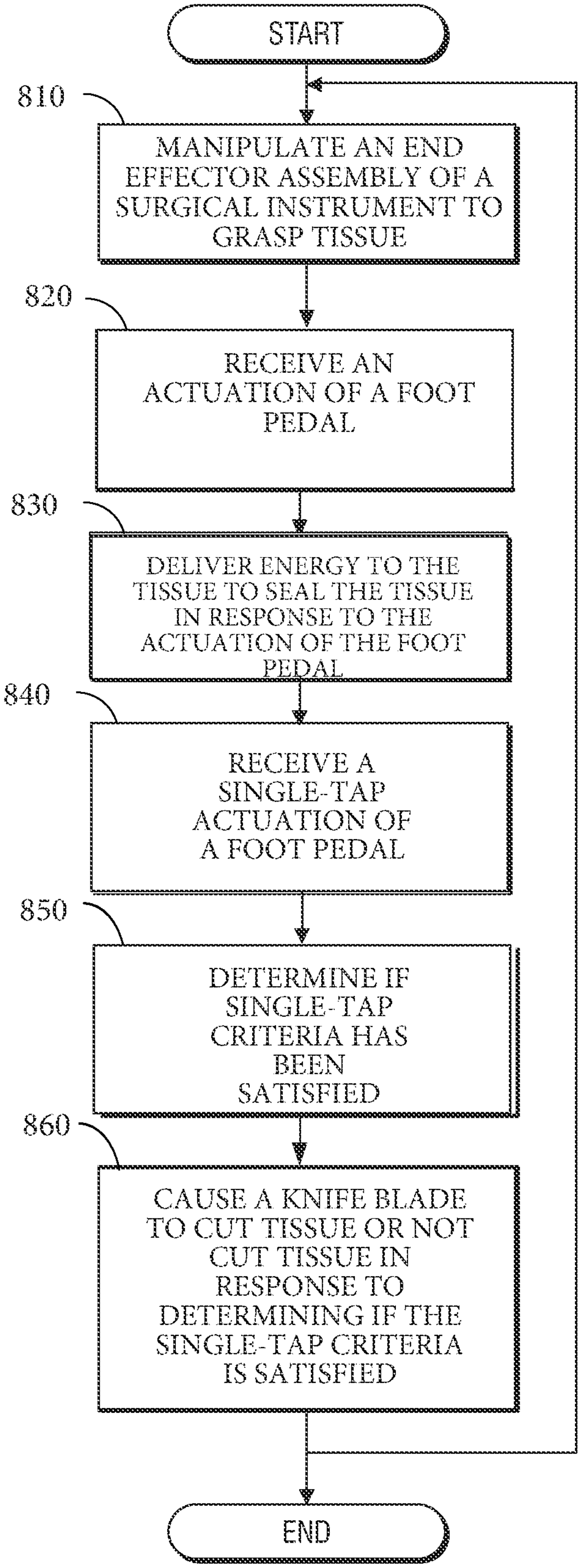
FIG. 8 is a flowchart outlining a method provided in accordance with an aspect of this disclosure.

Referring now to FIG. 8, one approach for the use of surgical instrument 110 is described. The end effector assembly 140 at block 810 is manipulated into position by the clinician via handle controllers 38*a* and 38*b* at surgical console 30 of surgical robotic system 10 such that tissue to be sealed and/or cut is disposed between jaw members 142, 144, with jaw members 142, 144 in the spaced-apart position. With tissue positioned between tissue-contacting surfaces 146, 148, surgical robotic system 10 actuates drive rod 1484 to pivot jaw member 142 toward jaw member 144 to move jaw members 142, 144 from the spaced-apart position to the approximated position to grasp tissue between tissue-contacting surfaces 146, 148. This may be caused by a clinician at surgical console 30 actuating one or both of handle controllers 38*a*, 38*b* (or one of foot pedals 36 into an actuated position). Once tissue is grasped between tissue-contacting surfaces 146, 148, the process proceeds to block 820.

At block 820, a first actuation of one of foot pedals 36 is received at surgical console 30. In response to the first actuation of the foot pedal, surgical robotic system 10 at block 830 causes controller 210 to signal power source 220 and/or RF output stage 230 to supply energy to tissue-contacting surfaces 146, 148 for conduction through tissue grasped therebetween to effect tissue sealing. In aspects of the disclosure, the first actuation of the foot pedal may include maintaining the foot pedal in an actuated position throughout blocks 820 and 830 until a tissue sealing cycle is determined to be complete, as described above.

At block 840, a single-tap actuation of one of the foot pedals 36 is received at surgical console 30 and, if at block 850 it is determined that the aforementioned single-tap criteria have been satisfied including receiving the single-tap actuation of one of the foot pedals 36 within the predetermined period of time following initiation of the tissue sealing cycle or following completion of the tissue sealing cycle, controller 210 causes motor output module 250 to communicate an output signal to surgical robotic system 10 to effect actuation of knife rod 1384 to reciprocate knife blade 147 between jaw members 142, 144 to cut tissue grasped between tissue-contacting surfaces 146, 148 at block 860. If it is determined that the aforementioned single-tap criteria have not been satisfied, either no output signal to effect actuation of knife rod 1384 is communicated to surgical robotic system 10 or an output signal is communicated to surgical robotic system 10 to not actuate knife rod 1384 at block 860. In aspects of the disclosure, the clinician may operate outside of the aforementioned single-tap criteria to effect actuation of the knife rod 1384, for example, by double-tapping one of the foot pedals 36.

In the scenario where the aforementioned single-tap criteria have not been satisfied, the process may deviate from the approach illustrated in FIG. 8 to achieve tissue sealing and cutting. For example, if the single-tap criteria are determined to not be satisfied at block 850, the clinician may be enabled to manually control tissue sealing and tissue cutting via actuation (e.g., double-tap) of one of the foot pedals 36.

In aspects of the disclosure, the actuation of the foot pedal received at block 820 may include the clinician at surgical console 30 maintaining the same foot pedal in an actuated position throughout blocks 820 and 830. In some aspects, at block 840, the clinician may single-tap the same foot pedal that was maintained in the actuated position throughout blocks 820 and 830 after the clinician releases that foot pedal to indicate that the tissue sealing cycle is completed. In some aspects, the clinician at block 840 may optionally single-tap a different foot pedal than that which was actuated throughout blocks 820 and 830.

In some aspects of the disclosure, once tissue has been sealed and cut, surgical robotic system 10 may, in response to actuation of one of the foot pedals 36 or actuation of one or both of handle controllers 38*a* and 38*b*, cause actuation of drive rod 1484 to pivot jaw member 142 away from jaw member 144 to move jaw members 142, 144 from the approximated position to the spaced-apart position to release the sealed and cut tissue from between tissue-contacting surfaces 146, 148. Once the sealed and cut tissue has been released, end effector assembly 140 may be repositioned such that, once tissue determined to be present and sufficiently positioned between jaw members 142, 144, the above-described process repeats itself. As can be appreciated, such a configuration allows for rapid and repeated tissue sealing and cutting, which is particularly advantageous for use in advancing through large volumes of tissue.

Figure 9:
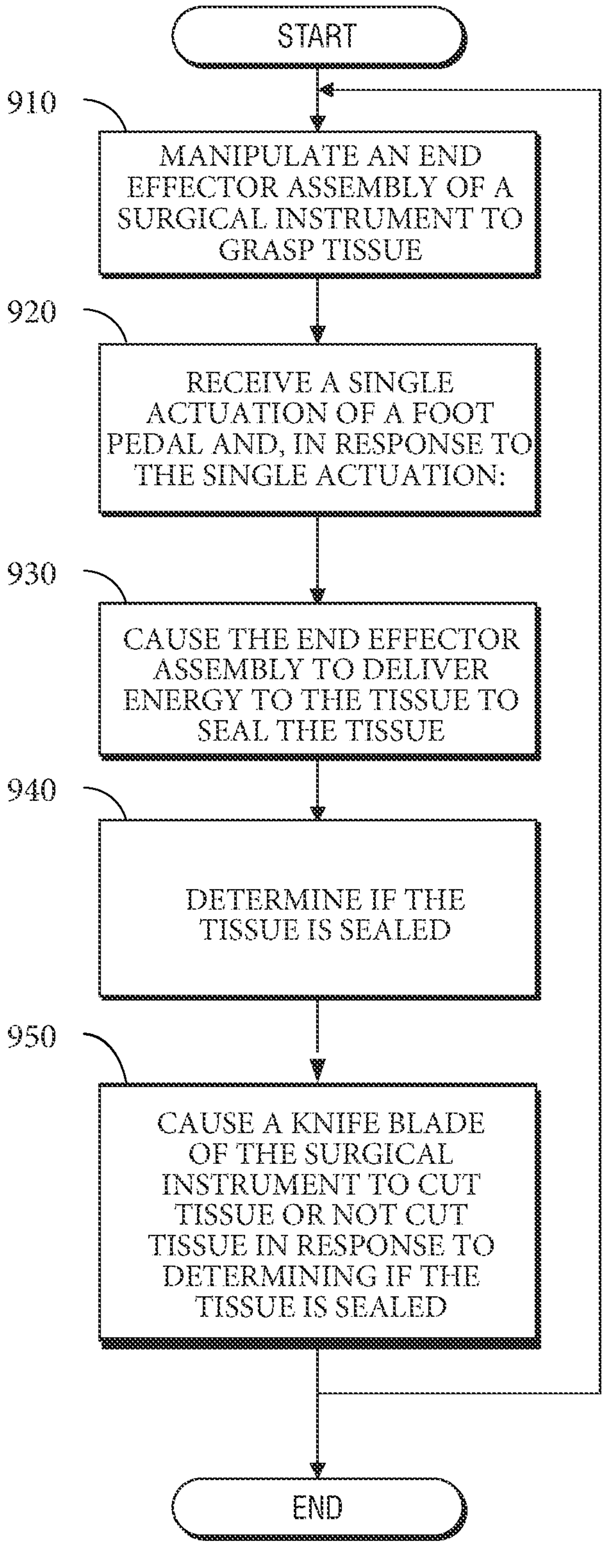
FIG. 9 is a flowchart outlining a method provided in accordance with another aspect of this disclosure.

Referring now to FIG. 9, an approach for the use of surgical instrument 110 in the auto-cut mode of operation is described. Generally, in order to activate surgical instrument 110 for use in one of the auto-cut mode of operation or the manual mode of operation, the user may select the operating mode via one or more suitable user inputs provided by surgical robotic system 10 (e.g., a user interface provided by display 23 of control tower 20, a user interface provided by first display 32 and/or second display 34 of surgical console 30), one or more inputs of energy source 200, and/or one or more inputs of surgical instrument 110. Once activated for use in the auto-cut mode of operation, end effector assembly 140 at block 910 is manipulated into position by the user via handle controllers 38*a* and 38*b* at the surgical console 30 of surgical robotic system 10 such that tissue to be sealed and/or cut is disposed between jaw members 142, 144, with jaw members 142, 144 in the spaced-apart position. With tissue positioned between tissue-contacting surfaces 146, 148, surgical robotic system 10 actuates drive rod 1484 to pivot jaw member 142 toward jaw member 144 to move jaw members 142, 144 from the spaced-apart position to the approximated position to grasp tissue between tissue-contacting surfaces 146, 148. This may be caused by the user at surgical console 30 actuating one or both of handle controllers 38*a*, 38*b* (or one of foot pedals 36 into an actuated position). Once tissue is grasped between tissue-contacting surfaces 146, 148, the process proceeds to block 920.

Optionally, a determination of whether tissue is present and sufficiently grasped between tissue-contacting surfaces 146, 148 may be made prior to the process proceeding to block 920 based on feedback received by sensor module 240 of energy source 200 from suitable sensors (not shown) associated with end effector assembly 140. The determination of whether tissue is present and sufficiently grasped between tissue-contacting surfaces 146, 148 is provided by controller 210 as feedback to surgical robotic system 10 and indicated to the user (e.g., via first display 32 of surgical console 30, second display 34 of surgical console 30, and/or display 23 of control tower 20).

At block 920, a single actuation of one of foot pedals 36 is received at surgical console 30. In response to the single actuation of the foot pedal, surgical robotic system 10 at block 830 causes controller 210 to signal power source 220 and/or RF output stage 230 to supply energy to tissue-contacting surfaces 146, 148 for conduction through tissue grasped therebetween to effect tissue sealing. In aspects of the disclosure, a single actuation of the foot pedal may include maintaining the foot pedal in an actuated position throughout any one or more blocks (e.g., blocks 920-950) of the illustrated approach of FIG. 9.

At block 940, in response to the single actuation of the foot pedal, it is determined if the grasped tissue through which the energy was conducted at block 930 is sealed. More specifically, during the application of energy to tissue-contacting surfaces 146, 148, as indicated at block 930, tissue property unit 244 of sensor module 240 monitors the impedance of tissue grasped between tissue-contacting surfaces 146, 148 (and/or other properties of tissue) to determine when an effective tissue seal has been established. The determination of whether an effective tissue seal has been established is provided by controller 210 as feedback to surgical robotic system 10 and indicated to the user (e.g., via first display 32 of surgical console 30, second display 34 of surgical console 30, and/or display 23 of control tower 20). Once it is determined if the tissue has been sealed, the process proceeds to block 950.

At block 950, in response to determining if the tissue is sealed at block 940 and in response to the single actuation of the foot pedal, knife blade 147 is either caused to cut the tissue or to not cut the tissue. In aspects of the disclosure, if it is determined at block 940 that the tissue is sealed, controller 210 causes motor output module 250 to communicate an output signal to surgical robotic system 10 to effect actuation of knife rod 1384 to reciprocate knife blade 147 between jaw members 142, 144 to cut tissue grasped between tissue-contacting surfaces 146, 148. If it is determined at block 940 that the tissue is not sealed, either no output signal to effect actuation of knife rod 1384 is communicated to surgical robotic system 10 or an output signal is communicated to surgical robotic system 10 to not actuate knife rod 1384. In aspects of the disclosure, determination of whether or not the tissue is sealed may include determining of various properties of the tissue. For example, factors such as the tissue bleeding excessively and/or the tissue being only partially sealed may contribute to a determination that the tissue is not sealed. In the scenario where tissue is determined to not be sealed, the process may deviate from the approach illustrated in FIG. 9 to achieve tissue sealing and cutting. For example, if the tissue is determined to not be sealed at block 940, the auto-cut mode may be deactivated and the manual mode of operation activated to enable the user to manually control tissue sealing and tissue cutting via actuation of the foot pedal. In aspects of the disclosure, deactivation of auto-cut mode and/or activation of manual mode may be effected either manually by the user or automatically by surgical robotic system 10 in response to a determination that the tissue is not sealed.

In aspects of the disclosure, the single actuation of the foot pedal received at block 920 may include the user at surgical console 30 maintaining the same foot pedal in an actuated position throughout blocks 920, 930, 940, and 950. In some aspects, at block 950, the user may re-actuate the same foot pedal 36 that was maintained in the actuated position at blocks 920, 930, and/or 940 after allowing the foot pedal 36 to move to an unactuated position in response to a determination that the tissue is not sealed at block 940. In some aspects, the user at block 950 may optionally actuate a different foot pedal 36 than that which was actuated at blocks 920, 930, and 940 in response to a determination that the tissue is not sealed at block 940.

In some aspects of the disclosure, feedback provided by knife drive sub-assembly 1300 of surgical robotic system 10 may indicate successful extension and retraction of knife blade 147 to cut tissue. The determination of whether knife blade 147 has been successfully extended and retracted may be indicated to the user (e.g., via first display 32 of surgical console 30, second display 34 of surgical console 30, and/or display 23 of control tower 20).

In some aspects of the disclosure, once tissue has been sealed and cut, surgical robotic system 10 may, in response to the received single actuation of the foot pedal at block 920, further cause actuation of drive rod 1484 to pivot jaw member 142 away from jaw member 144 to move jaw members 142, 144 from the approximated position to the spaced-apart position to release the sealed and cut tissue from between tissue-contacting surfaces 146, 148. Alternatively, the user may re-actuate the same foot pedal that was maintained in an actuated position at blocks 920, 930, 940, and/or 950 after allowing the foot pedal to move to an unactuated position once tissue is determined to be cut, e.g., as determined by feedback provided by knife drive sub-assembly 1300 of robotic surgical system 10. In some aspects, the user may optionally actuate a different foot pedal than that which was actuated at blocks 920, 930, 940, and/or 950 to cause pivoting of jaw member 142 away from jaw member 144 to move jaw members 142, 144 from the approximated position to the spaced-apart position to release the sealed and cut tissue from between tissue-contacting surfaces 146, 148.

Once the sealed and cut tissue has been released, end effector assembly 140 may be repositioned such that, once tissue determined to be present and sufficiently positioned between jaw members 142, 144, the above-described process repeats itself. As can be appreciated, such a configuration allows for rapid and repeated tissue sealing and cutting, which is particularly advantageous for use in advancing through large volumes of tissue.

It is also envisioned that surgical instrument 110 be capable of use in various combinations of the above-described automatic and manual modes of operation. That is, any of the operating steps of surgical instrument 110 may be automatically initiated or manually activated to achieve a desired configuration. For example, grasping of tissue (and initiating the supply of energy to the jaw members) may be acheived manually, while tissue sealing, cutting (mechanically or electrically) of tissue, and releasing the sealed and cut tissue may be performed automatically. Other suitable combinations are also contemplated. Additionally, rather than performing automatic actions, the above-described feedback based system may be utilized to indicate a current state of the process, for example, to indicate, e.g., via audible or visual indicators, that tissue is present between the jaw members, tissue sealing is complete, and/or that tissue cutting is complete.

It should be understood that various aspects disclosed herein may be combined in different combinations than the combinations specifically presented hereinabove and in the accompanying drawings. In addition, while certain aspects of this disclosure are described as being performed by a single module or unit for purposes of clarity, it should be understood that the techniques of this disclosure may be performed by a combination of units or modules associated with, for example, a surgical system.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical system, comprising:
- a robotic surgical system, including:
  - at least one motor;
  - at least one foot pedal; and
  - a controller in communication with the at least one foot pedal and configured to cause the at least one motor to provide an input based on actuation of the at least one foot pedal; and
- a surgical instrument in communication with the robotic surgical system, the surgical instrument including:
  - a pair of jaw members movable between a spaced-apart position and an approximated position and configured to deliver electrosurgical energy to tissue grasped between the pair of jaw members to seal the tissue when the pair of jaw members are in the approximated position;
  - a knife blade configured to extend through the pair of jaw members to cut tissue grasped between the pair of jaw members when the pair of jaw members are in the approximated position; and
  - a drive assembly configured to receive the input provided by the at least one motor, wherein the drive assembly is configured to cause:
    - the pair of jaw members to deliver energy to the tissue grasped between the pair of jaw members to seal the tissue in response to a first actuation of the at least one foot pedal; and
    - the knife blade to extend through the pair of jaw members to cut the tissue in response to:
      - a determination that the tissue has been sealed, wherein the determination that the tissue has been sealed is based on the first actuation of the at least one foot pedal and a termination of the first actuation of the at least one foot pedal in response to an indication that the tissue is sealed;
      - a determination that the pair of jaw members are maintained in the approximated position; and
      - a second actuation of the at least one foot pedal within a predetermined period of time following the first actuation of the at least one foot pedal.

2. The surgical system according to claim 1, wherein the first actuation of the at least one foot pedal includes maintaining the at least one foot pedal in an actuated position.

3. The surgical system according to claim 1, wherein the second actuation of the at least one foot pedal includes a single-tap of the at least one foot pedal.

4. The surgical system according to claim 1, wherein the predetermined period of time is about 15 seconds.

5. The surgical system according to claim 1, wherein the predetermined period of time is from about 0.5 seconds to about 15 seconds.

6. The surgical system according to claim 1, wherein the predetermined period of time is from about 0.75 seconds to about 15 seconds.

7. The surgical system according to claim 1, wherein the second actuation of the at least one foot pedal includes actuating the same foot pedal as the first actuation of the at least one foot pedal.

8. The surgical system according to claim 1, wherein the at least one foot pedal includes at least two foot pedals, and the second actuation of the at least one foot pedal includes actuating a different foot pedal than the foot pedal actuated by the first actuation of the at least one foot pedal.

9. The surgical system according to claim 1, wherein the determination that the pair of jaw members are maintained in the approximated position is based on a position of a drive rod configured to be actuated longitudinally to move the pair of jaw members between the spaced-apart and approximated positions.

10. The surgical system according to claim 1, wherein the robotic surgical system includes a handle controller configured to cause the pair of jaw members to transition between the spaced-apart position and the approximated position to grasp tissue between the pair of jaw members or release tissue from between the pair of jaw members.

11. The surgical system according to claim 1, further comprising an electrosurgical energy source configured to deliver the electrosurgical energy to the pair of jaw members.

12. The surgical system according to claim 11, wherein the electrosurgical energy source is configured to:
- determine that the tissue is sealed; and
- provide an indication that the tissue is sealed.

13. A method for operating a surgical instrument interfaced with a robotic surgical system to treat tissue, comprising:
- manipulating an end effector assembly of a surgical instrument to grasp tissue;
- receiving a first actuation of a first foot pedal;
- causing the end effector assembly to deliver energy to the tissue to seal the tissue in response to the first actuation;
- releasing the first foot pedal to terminate the first actuation in response to an indication that the tissue is sealed;
- receiving a second actuation of the first foot pedal or a second foot pedal; and
- causing a knife blade of the surgical instrument to cut the tissue or not cut the tissue based on:

a releasing of the first foot pedal to terminate the first actuation, wherein the releasing of the first foot pedal to terminate the first actuation indicates that the tissue is sealed;

a determination that the end effector is grasping the tissue; and receiving the second actuation within a predetermined period of time following the receiving of the first actuation of the first foot pedal.

14. The method according to claim 13, wherein receiving the first actuation of the first foot pedal includes maintaining the first foot pedal in an actuated position.

15. The method according to claim 13, wherein receiving the second actuation of the first or second foot pedal includes providing a single-tap actuation of the first or second foot pedal.

16. The method according to claim 13, wherein the predetermined period of time is about 15 seconds.

17. The method according to claim 13, wherein the predetermined period of time is from about 0.5 seconds to about 15 seconds.

18. The method according to claim 13, wherein the predetermined period of time is from about 0.75 seconds to about 15 seconds.

19. The method according to claim 13, wherein the determination that the end effector is grasping the tissue is based on a position of a drive rod configured to be actuated longitudinally to move the end effector between an open position and a closed position.

* * * * *